(12) United States Patent
Wright et al.

(10) Patent No.: US 10,870,625 B2
(45) Date of Patent: Dec. 22, 2020

(54) ZWITTERIONIC PROPARGYL-LINKED ANTIFOLATES USEFUL FOR TREATING BACTERIAL INFECTIONS

(71) Applicants: THE UNIVERSITY OF CONNECTICUT, Farmington, CT (US); United States of America as represented by the Department of Veterans Affairs, Syracuse, NY (US)

(72) Inventors: Dennis Wright, Storrs, CT (US); Amy C. Anderson; Eric Scocchera, Mansfield Center, CT (US); Narendran Gummudipundi Dayanandan, Mansfield Center, CT (US); Santosh Keshipeddy, Hamden, CT (US); Stephanie Reeve, Manchester, CT (US); Michael N. Lombardo, Manchester, CT (US); Michael Henry Cynamon, Dewitt, NY (US)

(73) Assignee: UNIVERSITY OF CONNECTICUT, Farmington, CT (US)

( * ) Notice: Subject to any disclaimer, the term of this patent is extended or adjusted under 35 U.S.C. 154(b) by 0 days.

(21) Appl. No.: 16/068,262

(22) PCT Filed: Jan. 9, 2017

(86) PCT No.: PCT/US2017/012702
§ 371 (c)(1),
(2) Date: Jul. 5, 2018

(87) PCT Pub. No.: WO2017/120575
PCT Pub. Date: Jul. 13, 2017

(65) Prior Publication Data
US 2019/0002413 A1 Jan. 3, 2019

Related U.S. Application Data

(60) Provisional application No. 62/276,494, filed on Jan. 8, 2016.

(51) Int. Cl.
| | |
|---|---|
| C07D 405/06 | (2006.01) |
| C07D 405/14 | (2006.01) |
| C07D 239/02 | (2006.01) |
| C07D 239/48 | (2006.01) |
| C07D 239/49 | (2006.01) |
| C07D 403/10 | (2006.01) |
| A61P 31/04 | (2006.01) |
| A61P 31/06 | (2006.01) |

(Continued)

(52) U.S. Cl.
CPC .......... *C07D 239/49* (2013.01); *A61K 31/505* (2013.01); *A61K 31/506* (2013.01); *A61P 31/04* (2018.01); *A61P 31/06* (2018.01); *C07D 239/48* (2013.01); *C07D 403/10* (2013.01); *C07D 405/06* (2013.01); *C07D 405/14* (2013.01)

(58) Field of Classification Search
CPC .. C07D 405/06; C07D 405/14; C07D 239/02; C07D 239/48
See application file for complete search history.

(56) References Cited

U.S. PATENT DOCUMENTS

| | | |
|---|---|---|
| 8,426,432 B2 | 4/2013 | Anderson et al. |
| 8,853,228 B2 | 10/2014 | Anderson et al. |
| 2015/0225353 A1 | 8/2015 | Wright et al. |

FOREIGN PATENT DOCUMENTS

| | | |
|---|---|---|
| WO | 2009025919 A2 | 2/2009 |
| WO | 2013070620 A1 | 5/2013 |

OTHER PUBLICATIONS

G-Dayanandan et al. (Journal of Medicinal Chemistry (2014), 57(6), 2643-2656).*

(Continued)

*Primary Examiner* — Bruck Kifle
(74) *Attorney, Agent, or Firm* — Cantor Colburn LLP

(57) ABSTRACT

The disclosure provides compounds of the formula I and the pharmaceutically acceptable salts thereof.

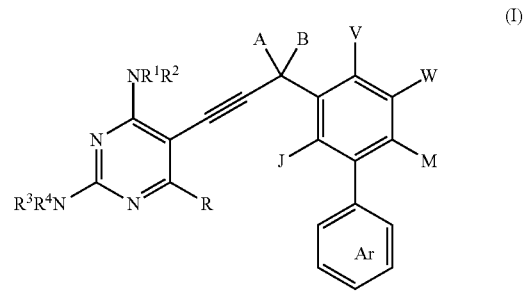

(I)

The variables, e.g. $R^1$, $R^2$, $R^3$, $R^4$, A, B, J, V, W, M, J and Ar are defined herein. The disclosure also provides pharmaceutical compositions comprising a compound or salt of formula I and a pharmaceutically acceptable carrier, methods of inhibiting dihydrofolate reductase (DHFR) in vitro or in vivo with a compound or salt of formula I, and methods of treating a bacterial infections, fungal infections, and protozoal infections with a compound or salt of formula I. A compound or salt of formula I can be the first and only active ingredient used in a pharmaceutical composition or method of this disclosure or may be combined with one or more additional active ingredients that are not compounds or salts of formula I.

18 Claims, 3 Drawing Sheets

(51) Int. Cl.
*A61K 31/505* (2006.01)
*A61K 31/506* (2006.01)

(56) References Cited

OTHER PUBLICATIONS

Adams et al., "PHENIX: a comprehensive Python-based system for macromolecular structure solution," Acta Crystallographica; 2010, pp. 213-221, Section D66.

Algul et al., "2,4-Diarnino-5-(2'-arylpropargyl)pyrimidine derivatives as new nonclassical antifolates for human dihydrofolate reductase inhibition," Journal of Molecular Graphics and Modelling; 2011, pp. 608-613, vol. 29, No. 5, Nov. 5, 2010.

Bolstad et al., "Structure-Based Approach to the Development of Potent and Selective Inhibitors of Dihydrofolate Reductase from Cryptosporidium," J. Med. Chem.; Nov. 13, 2008, pp. 6839-6852, vol. 51(21).

Fox et al., "Old yellow enzyme at 2 A resolution: overall structure, ligand binding, and comparison with related flavoproteins," Structure; Nov. 15, 1994, pp. 1089-1105, vol. 2.

Frey et al., "Prospective Screening of Novel Antibacterial Inhibitors of Dihydrofolate Reductase for Mutational Resistance," American Society for Microbiology—Antimicrobial Agents and Chemotherapy; Jul. 2012, pp. 3556-3562, vol. 56, No. 7.

Frey et al., "Towards the understanding of resistance mechanisms in clinically isolated trimethoprim-resistant, methicillin-resistant *Staphylococcus aureus* dihydrofolate reductase," Journal of Structural Biology; 2010, pp. 93-97, vol. 170.

G-Dayanandan et al., "Propargyl-Linked Antifolates are Dual Inhibitors of Candida albicans and Candida glabrata," Journal of Medicinal Chemistry; 2014, pp. 2643-2656, vol. 57(6).

International Preliminary Report on Patentability; International Application No. PCT/US2017/012702; International Filing Date: Jan. 9, 2017; dated Jul. 10, 2018; 9 pages.

International Search Report for International Application No. PCT/US2017/012702, International Filing Date: Jan. 9, 2017, dated Feb. 24, 2017, 8 pages.

Liu et al., "Towards New Antifolates Targeting Eukaryotic Opportunistic Infections," Eukaryotic Cell; Apr. 2009, pp. 483-486, vol. 8, No. 4.

Lombardo et al, "Crystal Structures of Trimethoprim-Resistant DfrA1 Rationalize Potent Inhibition by Propargyl-Linked Antifolates," ACS Infectious Diseases; 2016, pp. 149-156, vol. 2.

McCoy et al., "Phaser crystallographic software," Journal of Applied Crystallography; 2007, pp. 658-674, vol. 40.

Paulsen et al., "In vitro biological activity arid structural analysis of 2,4-diamino-5-(2'-arylpropargyl)pyrimidine inhibitors of Candida albicans," Bioorganic & Medicinal Chemistry; 2009, pp. 4866-4872, vol. 17(14).

Paulsen et ai., "Structural analysis of the active sites of dihydrofolate reductase from two species of Candida uncovers ligand-induced conformational changes shared among species," Bioorganic & Medicinal Chemistry Letters; 2013, pp. 1279-1284, vol. 23(5).

Reeve et al., "MRSA Isolates from United States Hospitals Carry dfrG and dfrK Resistance Genes and Succomb to Propargyl-Linked Antifolates," Cell Chemical Biology, 2016, pp. 1458-1467, vol. 23(12).

Viswanathan et al., "Towards New Therapeutics for Skin and Soft Tissue Infections: Propargyl-Linked Antifolates Are Potent Inhibitors of MRSA and *Streptococcus pyogenes*," PLoS ONE; Feb. 7, 2012, pp. 1-9, vol. 7, Issue 2, e29434.

Written Opinion for International Application No. PCT/US2017/012702, International Filing Date Jan. 9, 2017, dated Feb. 24, 2017, 9 pages.

Zhou et al., "Acetylenic Linkers in Lead Compounds: A Study of the Stability of the Propargyl-Linked Antifolates," Drug Metabolism and Disposition; 2012, pp. 2002-2008, vol. 40, No. 10.

Hajian, Behnoush et al.; "Propargyl-Linked Antifolates Are Potent Inhibitors of Drug-Sensitive and Drug-Resistant *Mycobacterium tuberculosis*"; PLOS One; Aug. 31, 2016: p. 1-13.

Scocchera, Eric et al.; "Charged Nonclassical Antifolates with Activity Against Gram-Positive and Gram-Negative Pathogens"; ACS Medicinal Chemistry Letters, vol. 7; 2016: p. 692-696.

White; P. Lewis et al.; "Diagnosis and management of Pneumocystis jirovecii infection"; Expert Review of Anti-infective Therapy, vol. 15, No. 5; 2017: p. 435-447.

\* cited by examiner

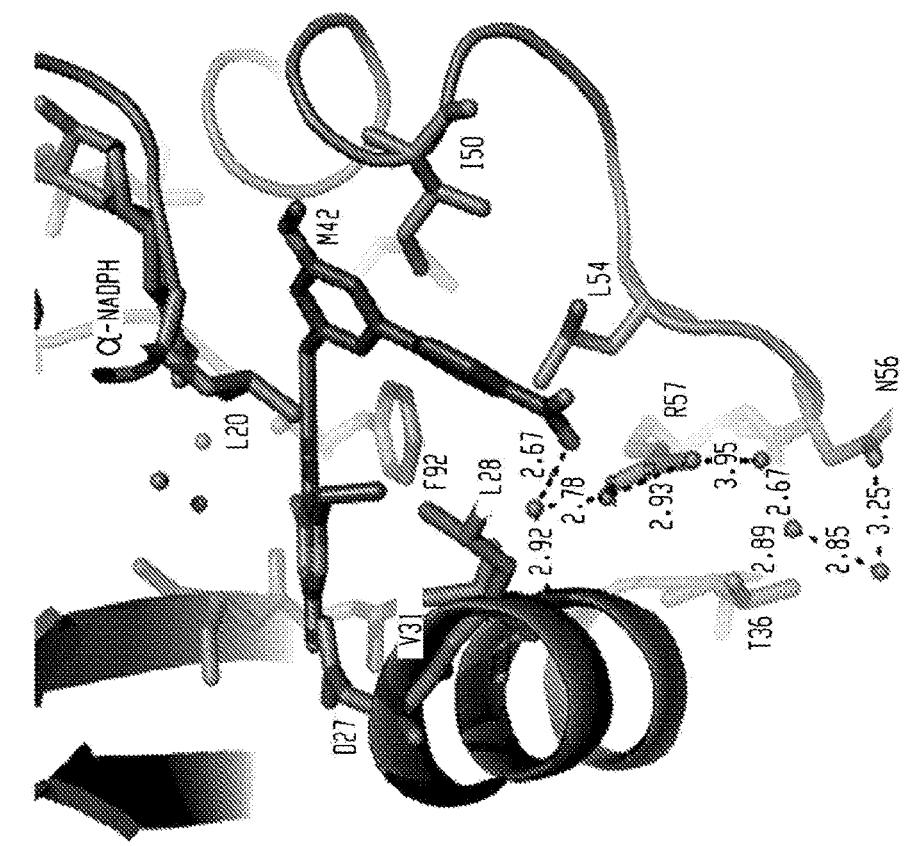
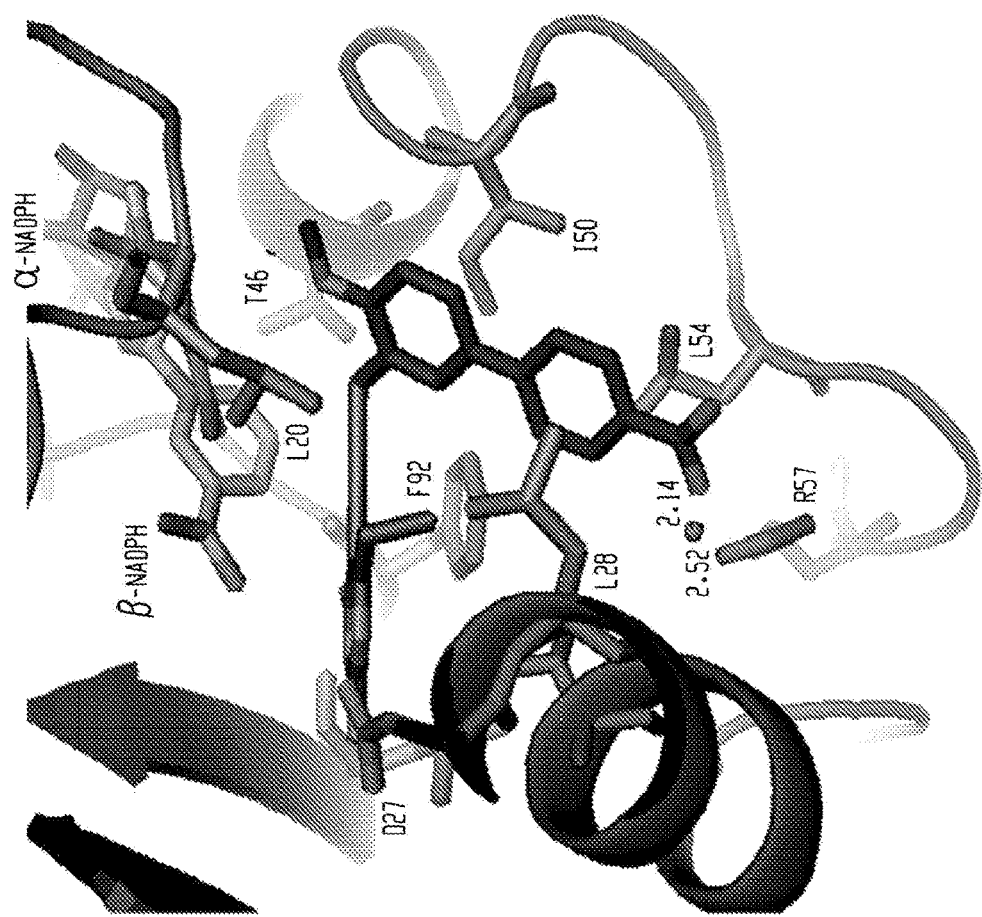
Fig. 2A
Fig. 2B

ZWITTERIONIC PROPARGYL-LINKED ANTIFOLATES USEFUL FOR TREATING BACTERIAL INFECTIONS

This application is a U.S. National Stage Application of PCT/US 17/12702 filed Jan. 9, 2017, which claims priority from U.S. Provisional Application No. 62/276,494, filed Jan. 8, 2016, both of which are hereby incorporated by reference in their entirety.

BACKGROUND

The essential metabolic enzyme dihydrofolate reductase (DHFR) has been a successfully and widely targeted protein for both oncology and infectious disease indications, delivering efficacious drugs such as methotrexate (MTX), trimethoprim (TMP) and pemetrexed (PMX). Its natural substrates, folic acid or dihydrofolate, possess a weakly basic pterin ring and a negatively charged glutamate extension that are critical for binding of the enzyme. Several crystal structures with different species of DHFR reveal that classical antifolates such as methotrexate (FIG. 1) and pemetrexed mimic these motifs of the substrate with a basic nitrogenous ring that forms strong contacts with an acidic residue in the active site and a glutamate moiety that forms extensive ionic interactions with a basic amino acid (Arg 57 in S. aureus DHFR. As substrate mimics, classical antifolates often possess very high affinity for DHFR. For example, methotrexate inhibits human, Escherichia coli and Staphylococcus aureus DHFR with $K_i$ values of 3.4 pM, 1 pM, and 1 nM, respectively.

However, as these classical antifolates are highly negatively charged at physiological pH, they do not appear to passively diffuse and require active transport through human cell membranes to obtain physiological concentrations. Furthermore, they are subsequently polyglutamylated in the cell for optimal cellular retention and enzyme affinity. Currently, all approved anticancer DHFR inhibitors are categorized as classical antifolates. In contrast, as bacteria rely on the de novo synthesis of folate cofactors, they do not possess folic acid transporters. Therefore, classical antifolates can only rely on passive diffusion through the membrane to achieve antibacterial effects, hence the MIC value of the very potent enzyme inhibitor MTX against wild-type Gram-negative E. coli is over 1 mM. Even when efflux pumps are genetically deleted, the MIC value is 64-256 μM, demonstrating that the compound has limited permeability in addition to being an efflux substrate. Similarly, against the Gram-positive methicillin-resistant S. aureus (MRSA), methotrexate has an $MIC_{50}$ of 20 μg/mL or an $MIC_{90}$ of 100 μg/mL. In contrast, the weakly basic, non-classical antifolate trimethoprim (FIG. 1) with weaker DHFR inhibition ($IC_{50}$ values of 23 nM and 20 nM) is in fact a potent antibacterial against both MRSA and E. coli (MIC values of 0.3125 μg/mL) and is a first line agent with sulfamethoxazole against both Gram-negative and Gram-positive infections.

It has been appreciated that zwitterionic compounds possessing a single acidic functional group, such as fluoroquinolones (FIG. 1), which target bacterial gyrases, or tetracyclines that target microbial ribosomes, show utility against both Gram-positive and Gram-negative bacteria. The activity of these compounds may relate to their lower $clogD_{7.4}$ values (−1.35 for ofloxacin) and larger contributions to increased polarity under neutral conditions.

Propargyl-linked antifolates (PLAs) act as DHFR inhibitors for both Gram-positive and Gram negative bacteria. The inventors and others have previously reported PLAs with very potent MIC values against MRSA and Streptococcus pyogenes (Frey, K. M., et al., Am. Soc. Microbiol. (2012) 56(7): 3556-3562, Keshipeddy, S., et al., Synfacts (2015) 11(10): 1026; Viswanathan, K., et al., PloS One (2012) http://dx.doi.org/10.1371/journal.pone.0029434) and good inhibition of Klebsiella pneumoniae (Lamb, K. M., et al., Am. Soc. Microbiol. (2014) 58 (12) 7484-7491. The need exists for DHFR inhibitors with high potency again Gram-positive and Gram-negative bacteria. This disclosure provides such inhibitors and additional advantages, which are discussed below.

SUMMARY

The disclosure provides compounds of the formula I and the pharmaceutically acceptable salts thereof.

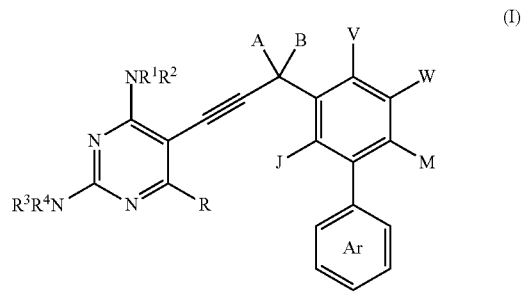

Within formula I the variables, e.g. R, $R^1$-$R^4$, A, B, J, M, V, W, and Ar, carry the following definitions.

R is H, hydroxyl, $C_1$-$C_6$alkyl, or $C_1$-$C_6$alkoxy.

$R^1$, $R^2$, $R^3$, and $R^4$ are independently chosen from H, $C_1$-$C_6$alkyl, and cycloalkyl.

A and B are independently chosen from H, hydroxyl, $C_1$-$C_6$alkyl, and $C_1$-$C_6$alkoxy.

One of V and W is methoxy and the other is chosen from H, $C_1$-$C_6$alkyl, and $C_1$-$C_6$alkoxy.

J and M are independently selected from H, halogen, hydroxyl, nitro, cyano, —COOH, —CHO, —CONH₂, cycloalkyl, or $C_1$-$C_6$alkyl in which any methylene (—CH₂) is optionally replaced by O, NH, N($C_1$-$C_6$alkyl), S, SO₂, C(O)O, OC(O), or C(O), and which is optionally substituted with hydroxyl, amino, or halogen.

W and M may be joined to form a 5- or 6-membered carbocyclic ring or a 5- or 6-membered heterocyclic ring that contains 1, 2, or 3 heteroatoms independently chosen from N, O, and S.

The Ar ring is a phenyl, pyridyl, or pyrimidinyl ring substituted with at least one —COOH or —CH₂COOH group and optionally substituted with one or more substituents independently chosen from halogen, hydroxyl, amino, $C_1$-$C_6$alkyl, $C_1$-$C_6$alkoxy, $C_1$-$C_2$haloalkyl, and $C_1$-$C_2$haloalkoxy.

The disclosure provides a pharmaceutical composition comprising a compound of formula I or salt thereof and a pharmaceutically acceptable carrier.

The disclosure provides a method of inhibiting dihydrofolate reductase (DHFR) in vitro or in vivo comprising contacting the DHFR with a compound of formula I or salt thereof.

The disclosure also provides a method of treating a bacterial infection, a fungal infection, or a protozoal infection in a patient comprising administering a therapeutically effective amount of a compound of formula I or salt thereof to the patient.

The disclosure provides combination formulations and methods of treatment in which the compound of formula I or salt thereof is a first active agent which is combined with or administered with a second active agent that is not a compound or salt of formula I.

DETAILED DESCRIPTION

Terminology

Figure 1:
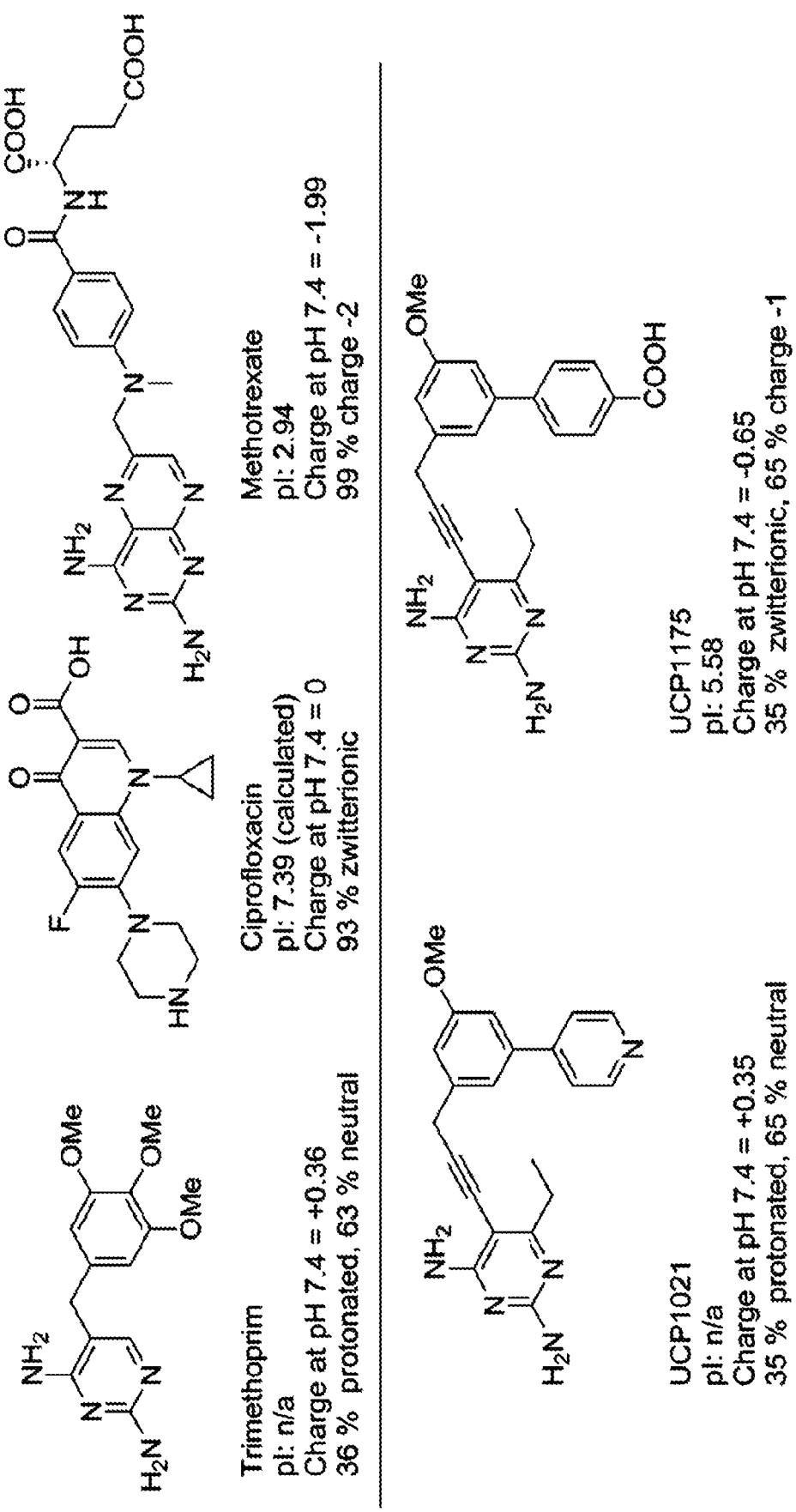
FIG. 1. Antibacterial agents effective against Gram-positive or Gram-negative bacteria with relevant physiological properties. A previous PLA, UCP1021, is compared to a COOH-PLA.

Compounds are described using standard nomenclature. Unless defined otherwise, all technical and scientific terms used herein have the same meaning as is commonly understood by one of skill in the art to which this disclosure belongs. Unless clearly contraindicated by the context, each compound name includes the free acid or free base form of the compound as well as all pharmaceutically acceptable salts, solvates, and hydrates of the compound.

The term "formula I" encompasses all compounds that satisfy formula I, including any enantiomers, racemates and stereoisomers, as well as all pharmaceutically acceptable salts, solvates, and hydrates of such compounds. "Formula I" includes all subgeneric groups of formula I unless clearly contraindicated by the context in which this phrase is used.

The terms "a" and "an" do not denote a limitation of quantity, but rather denote the presence of at least one of the referenced item. The term "or" means "and/or". The open-ended transitional phrase "comprising" encompasses the intermediate transitional phrase "consisting essentially of" and the close-ended phrase "consisting of." Claims reciting one of these three transitional phrases, or with an alternate transitional phrase such as "containing" or "including" can be written with any other transitional phrase unless clearly precluded by the context or art. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to for illustration and does not pose a limitation on the scope of the disclosure unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this disclosure belongs.

Compounds of formula I include all compounds of formula I having isotopic substitutions at any position. Isotopes include those atoms having the same atomic number but different mass numbers. By way of general example, and without limitation, isotopes of hydrogen include tritium and deuterium and isotopes of carbon include $^1C$, $^{13}C$, and $^{14}C$. In some embodiments, any one or more hydrogen atoms are replaced with deuterium atoms.

An "active agent" means a compound (including a compound disclosed herein), element, or mixture that when administered to a patient, alone or in combination with another compound, element, or mixture, confers, directly or indirectly, a physiological effect on the subject. The indirect physiological effect may occur via a metabolite or other indirect mechanism. The "active agent" may also potentiate, or make more active another active agent. For example the compounds of formula I may act directly to kill bacteria or inhibit bacterial growth or may potentiate the activity of other antibacterial compounds when given in combination with another antibacterial compound, for example by lowering the MIC of the other antibacterial compound.

A dash ("-") that is not between two letters or symbols is used to indicate a point of attachment for a substituent. For example, —C(O)NH$_2$ is attached through carbon of the keto C(O) group.

"Alkyl" is a branched or straight chain saturated aliphatic hydrocarbon group, having the specified number of carbon atoms, generally from 1 to about 8 carbon atoms. The term $C_1$-$C_6$-alkyl as used herein indicates an alkyl group having from 1, 2, 3, 4, 5, or 6 carbon atoms. Other embodiments include alkyl groups having from 1 to 6 carbon atoms, 1 to 4 carbon atoms or 1 or 2 carbon atoms, e.g. $C_1$-$C_8$-alkyl, $C_1$-$C_4$-alkyl, and $C_1$-$C_2$-alkyl. Examples of alkyl include, but are not limited to, methyl, ethyl, n-propyl, isopropyl, n-butyl, 3-methylbutyl, t-butyl, n-pentyl, and sec-pentyl.

"Cycloalkyl" is a saturated hydrocarbon ring group, having the specified number of carbon atoms. Monocyclic cycloalkyl groups typically have from 3 to about 8 carbon ring atoms or from 3 to 6 (3, 4, 5, or 6) carbon ring atoms. Cycloalkyl substituents may be pendant from a substituted nitrogen, oxygen, or carbon atom, or a substituted carbon atom that may have two substituents may have a cycloalkyl group, which is attached as a spiro group. Examples of cycloalkyl groups include cyclopropyl, cyclobutyl, cyclopentyl, and cyclohexyl.

"Halo" or "halogen" indicates any of fluoro, chloro, bromo, and iodo.

"Haloalkyl" indicates both branched and straight-chain alkyl groups having the specified number of carbon atoms, substituted with 1 or more halogen atoms, up to the maximum allowable number of halogen atoms. Examples of haloalkyl include, but are not limited to, trifluoromethyl, difluoromethyl, 2-fluoroethyl, 2,2,2-trifluoroethyl, and penta-fluoroethyl.

"Haloalkoxy" indicates a haloalkyl group as defined herein attached through an oxygen bridge (oxygen of an alcohol radical).

The term "substituted," as used herein, means that any one or more hydrogens on the designated atom or group is replaced with a selection from the indicated group, provided that the designated atom's normal valence is not exceeded. When the substituent is oxo (i.e., =O) then 2 hydrogens on the atom are replaced. When an oxo group substitutes a heteroaromatic moiety, the resulting molecule can sometimes adopt tautomeric forms. For example a pyridyl group substituted by oxo at the 2- or 4-position can sometimes be written as a pyridine or hydroxypyridine. Combinations of substituents and/or variables are permissible only if such combinations result in stable compounds or useful synthetic intermediates. A stable compound or stable structure is meant to imply a compound that is sufficiently robust to survive isolation from a reaction mixture and subsequent formulation into an effective therapeutic agent. Unless otherwise specified, substituents are named into the core structure. For example, it is to be understood that aminoalkyl means the point of attachment of this substituent to the core structure is in the alkyl portion and alkylamino means the point of attachment is a bond to the nitrogen of the amino group.

A "dosage form" means a unit of administration of an active agent. Examples of dosage forms include tablets, capsules, injections, suspensions, liquids, emulsions, creams, ointments, suppositories, inhalable forms, transdermal forms, and the like.

"Pharmaceutical compositions" are compositions comprising at least one active agent, such as a compound or salt, solvate, or hydrate of Formula (I) or a prodrug thereof, and at least one other substance, such as a carrier. Pharmaceutical compositions optionally contain one or more additional active agents. When specified, pharmaceutical compositions meet the U.S. FDA's GMP (good manufacturing practice) standards for human or non-human drugs. "Pharmaceutical combinations" are combinations of at least two active agents which may be combined in a single dosage form or provided together in separate dosage forms with instructions that the active agents are to be used together to treat a disorder, such as a Gram-negative bacterial infection.

"Pharmaceutically acceptable salts" includes derivatives of the disclosed compounds in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Salts of the present compounds further include solvates of the compounds and of the compound salts.

Examples of pharmaceutically acceptable salts include, but are not limited to, mineral or organic acid salts of basic residues such as amines or nitrogen-containing heteroaryl rings (e.g. pyridine, quinoline, isoquinoline); alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, $HO_2C—(CH_2)n-CO_2H$ where n is 0-4, and the like. Lists of additional suitable salts may be found, e.g., in G. Steffen Paulekuhn, et al., *Journal of Medicinal Chemistry* 2007, 50, 6665 and *Handbook of Pharmaceutical Salts: Properties, Selection and Use*, P. Heinrich Stahl and Camille G. Wermuth Editors, Wiley-VCH, 2002.

The term "carrier" applied to pharmaceutical compositions/combinations of the disclosure refers to a diluent, excipient, or vehicle with which an active compound is provided.

A "patient" is a human or non-human animal in need of medical treatment. In some embodiments the patient is a human patient.

"Providing" means giving, administering, selling, distributing, transferring (for profit or not), manufacturing, compounding, or dispensing.

"Treatment," as used herein includes providing a compound of this disclosure such as a compound of Formula I, either as the only active agent or together with at least one additional active agent sufficient to: (a) inhibit the disease, i.e. arresting its development; and (b) relieve the disease, i.e., causing regression of the disease and in the case of a bacterial infection to eliminate or reduce the virulence of the infection in the subject. "Treating" and "treatment" also means providing a therapeutically effective amount of a compound of the disclosure as the only active agent or together with at least one additional active agent to a subject having or susceptible to a bacterial infection. "Prophylactic treatment" includes administering an amount of a compound of the disclosure sufficient to significantly reduce the likelihood of a disease from occurring in a subject who may be predisposed to the disease but who does not have it.

A "therapeutically effective amount" of a pharmaceutical composition/combination is an amount effective, when administered to a subject, to provide a therapeutic benefit, such as to decrease the morbidity and mortality associated with bacterial infection and/or effect a cure. In certain circumstances a subject suffering from a microbial infection may not present symptoms of being infected. Thus a therapeutically effective amount of a compound is also an amount sufficient to significantly reduce the detectable level of microorganism in the subject's blood, serum, other bodily fluids, or tissues. The disclosure also includes, in certain embodiments, using compounds of the disclosure in prophylactic treatment and therapeutic treatment. In the context of prophylactic or preventative treatment, a "therapeutically effective amount" is an amount sufficient to significantly decrease the incidence of or morbidity and mortality associated with bacterial infection. For example, prophylactic treatment may be administered when a subject is known to be at enhanced risk of bacterial infection, such cystic fibrosis or ventilator patients. A significant reduction is any detectable negative change that is statistically significant in a standard parametric test of statistical significance such as Student's T-test, where p<0.05.

Compound Description

The disclosure provides a class of propargyl-linked antifolates (PLAs) as inhibitors of DHFR for both Gram-positive and Gram-negative bacteria. PLAs are characterized as weakly basic non-classical antifolates that passively diffuse through membranes and potently inhibit the DHFR enzyme, often inhibiting the growth of bacterial cells with sub-micromolar MIC values. The inventors and others have previously achieved very potent MIC values against MRSA and *Streptococcus pyogenes* and good inhibition of *Klebsiella pneumoniae*. This disclosure provides zwitterionic PLAs and enantiomerically pure compounds having contacts typically made by the negatively charged glutamate tail, while maintaining or increasing bacterial cell permeability, we designed. Evaluation of enzyme inhibition and high resolution crystal structures with the *S. aureus* DHFR enzyme reveals that the carboxylic acid moiety forms key interactions with an arginine residue in the active site. The incorporation of this new high affinity contact may also provide compensatory interactions to offset the effects of known resistance conferring mutations.

Certain compounds of this disclosure potently inhibit MRSA. For example, certain compounds of this disclosure exhibit MIC values of approximately 1 ng/mL against these MRSA. Certain compounds of the disclosure also inhibit *E. coli*, with MIC values of 10 g/mL or less. Certain compounds of the disclosure also possess excellent drug-like properties. These properties can include, for example, not inhibiting the growth of human cell lines, not inhibiting critical CYP enzymes such as CYP3A4 and CYP2D6, and having a long half-life in microsomal stability assays.

At neutral pH the zwitterionic PLAs of this disclosure partition into two primary species: both are deprotonated at the carboxylate group. The pyrimidine ring is protonated in 35% of the species, forming a zwitterionic inhibitor; the remainder possess a neutral pyrimidine ring, yielding a negatively charged molecule. In certain embodiments the carboxylic acid forms hydrogen bonds with the conserved acidic residue (Asp 27 in *S. aureus* DHFR [SaDHFR]) and Arginine (Arg 57 in SaDHFR) in the active site, respectively. The disclosure provides COOH-PLAs with a $C_6$-ethyl diaminopyrimidine ring, either unsubstituted or methyl-substituted at the propargylic position, and a biphenyl system with either 2' or 3'-methoxy substituents. Any inhibitors synthesized with propargylic substitutions were prepared as enantiomerically pure entities.

Structure-activity analysis of the placement of the carboxylic acid group shows that while the ortho and meta placement yielded the greatest selectivity over the human enzyme, placement in the para position yields the highest affinity to the pathogenic enzymes. In SaDHFR, moving the COOH from para to meta or ortho results in a 5- and 12-fold loss in activity, respectively. Activity against EcDHFR decreases 6-fold when the carboxylic acid is moved from the para to meta position but only 2.2-fold when moved to the ortho position.

MIC values were maintained between wild-type and porin knockout strains (ΔompF and ΔompC), indicating that the compounds are passively diffused into the cells. The extraordinary activity in the Gram-positive bacteria indicates that negatively charged functionality can be incorporated in the molecules to create key contacts with the enzyme without compromising cellular penetration, as with methotrexate. Alternatively in Gram-negative bacteria, the highly negative lipopolysaccharide barrier may mitigate the penetration of the negatively charged population of PLAs by electrostatic repulsion.

Certain PLAs of this disclosure are active against *Myobacterium tuberculosis* (Mtb) DHFR. DHFR is not currently invoked for TB therapy. Methotrexate, pyrimethamine and trimetrexate, clinically approved antifolates, are potent inhibitors of the MtbDHFR enzyme but fail to inhibit the growth of Mtb, most likely due to an inability to permeate the lipid-rich cell wall. Certain PLAs of this disclosure inhibit the MtbDHFR enzyme activity and also inhibit the growth of live Mtb. Several of the compounds potently inhibit the growth of Mtb with MIC values less than 1 μg/mL. Certain compounds of the disclosure are very potent inhibitors of the growth of MDR- and XDR-TB strains and are not subject to cross-resistance with other known mechanisms.

Certain PLAs of the disclosure are active against trimethoprim-sulfamethoxazole resistant *Staphylococcus aureus* (MRSA) infections, especially those associated with community-acquired MRSA.

Trimethoprim inhibits dihydrofolate reductase while sulfamethoxazole inhibits dihydropteroate synthase. Both of these essential enzymes are involved in the folate biosynthetic pathway, which is critical for the creation of one-carbon donors in metabolism. While this combination has had wide success, resistant strains have become common. Mutation of the dfrB chromosomal gene is a principal mode of trimethoprim resistance. Additional mechanisms of resistance include the acquisition of plasmid-encoded trimethoprim-resistant DHFRs encoded by the genes dfrA, also called S1 DHFR, dfrG and dfrKs. Point mutations in dfrB confer resistance with MIC values ≤256≤g/mL; acquisition of S1 DHFR confers greater levels of resistance with MIC values ≥512≥g/mL.

Analysis of several resistant clinical isolates shows that the mutation F98Y is highly prevalent, especially in combination with secondary mutations, H149R or H30N. The $IC_{50}$ value for TMP is increased ~400-fold with the Sa(F98Y) enzyme and reported a crystal structure of the SaDHFR enzyme with the F98Y mutation bound to NADPH, the cofactor, and dihydrofolate, the substrate. The S1 DHFR protein natively includes a tyrosine at the 98 position as well as two other key mutations: G43A and V31I, relative to TMP-sensitive *S. epidermis*. Incorporation of G43A and F98Y has been shown to confer TMP resistance. Overall, studies of resistant strains confirm that new generations of antifolates targeting *S. aureus* DHFR must inhibit the mutant forms of the enzyme, including chromosomal mutants and plasmid-encoded resistant forms, in addition to the wild-type enzyme.

A full characterization of PLA-resistant single- and double-step mutants of *S. aureus* and show the acquisition of key clinical mutations: F98Y, H30N, H149R, F98Y/H30N and F98Y/H149R, albeit at lower mutational frequencies, that also confer resistance to TMP. Certain PLA compounds disclosed herein very potently inhibit both single and double mutant enzymes as well as wild-type and mutant *S. aureus* strains.

In summary, this new series of compounds demonstrates how the use of a carboxylate moiety to mimic one of the key interactions common to classical antifolates can be incorporated into the propargyl-linked antifolate architecture without compromising the ability to gain access to the target enzyme, DHFR. The preparation and evaluation of eight inhibitors show that the compounds have high enzyme affinity and increased antibacterial activity against MRSA and *E. coli* relative to earlier PLAs. High resolution crystal structures of two compounds with *S. aureus* DHFR reveal that affinity is enhanced by water-mediated contacts between the carboxylate and Arg 57 in the active site. Additional profiling supports the development of these compounds as antibacterial candidates.

The disclosure provides compounds of formula I, and the pharmaceutically acceptable salts thereof.

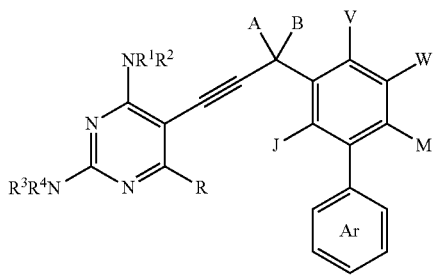

The variables in formula I (e.g. r, $R^1$-$R^4$, A, B, W, M, and J) can carry the definitions set forth in the SUMMARY section. Additionally these variables can carry any of the definitions set forth below.

The disclosure includes all combinations of variable definitions set forth in this specification so long as a stable compound is formed. The disclosure includes the following embodiments in which:

(1) R is methyl or ethyl; A is hydrogen; B is hydrogen or $C_1$-$C_6$alkyl; and one of V and W is methoxy and the other is H.

(2) $R_1$, $R_2$, $R_3$, and $R_4$ are H.

(3) J and M are independently selected from H, halogen, hydroxyl, $C_1$-$C_6$alkyl, $C_1$-$C_6$alkoxy, $C_1$-$C_2$haloalkyl, and $C_1$-$C_2$haloalkoxy.

(4) A is H and B is methyl.

(5) J and M are both H.

(6) Ar ring is substituted with one —COOH substituent in the para position and optionally substituted with one or more substituents independently chosen from halogen, hydroxyl, amino, $C_1$-$C_6$alkyl, $C_1$-$C_6$alkoxy, $C_1$-$C_2$haloalkyl, and $C_1$-$C_2$haloalkoxy.

(7) Ar ring is substituted with one —COOH substituent in the meta position and optionally substituted with one or more substituents independently chosen from halogen, hydroxyl, amino, $C_1$-$C_6$alkyl, $C_1$-$C_6$alkoxy, $C_1$-$C_2$haloalkyl, and $C_1$-$C_2$haloalkoxy.

(8) The Ar ring is substituted with one —COOH substituent in the ortho position and optionally substituted with one or more substituents independently chosen from halogen, hydroxyl, amino, $C_1$-$C_6$alkyl, $C_1$-$C_6$alkoxy, $C_1$-$C_2$haloalkyl, and $C_1$-$C_2$haloalkoxy.

(9) The Ar ring is a substituted phenyl ring. It may have any of the substituents listed in other embodiment for the Ar ring.

(10) R is methyl or ethyl; A is hydrogen; B is hydrogen or $C_1$-$C_6$alkyl; and W and M are joined to form a 5-membered heterocyclic ring containing 2 oxygen atoms.

(11) The disclosure includes the following compounds of formula I and their pharmaceutically acceptable salts:

(12) The disclosure includes a compound of formula I-A or a pharmaceutically acceptable salt thereof, wherein the compound is selected from the compounds listed in TABLE 1.

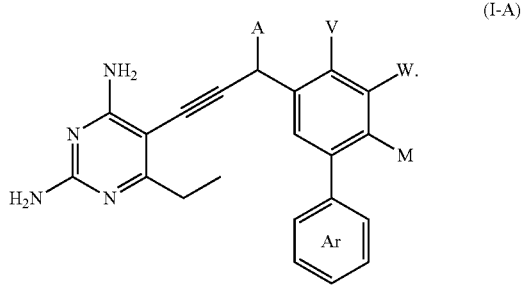

TABLE 1

| Cpd | A | V | W | M | Ar |
|---|---|---|---|---|---|
| 13 | H | OCH$_3$ | H | H | o-COOH phenyl |
| 14 | H | OCH$_3$ | H | H | m-COOH phenyl |
| 15 | H | OCH$_3$ | H | H | p-COOH phenyl |
| 16 | H | H | OCH$_3$ | H | p-COOH phenyl |
| 29 | S—CH$_3$ | OCH$_3$ | H | H | p-COOH phenyl |
| 30 | R—CH$_3$ | OCH$_3$ | H | H | p-COOH phenyl |
| 31 | R—CH$_3$ | H | OCH$_3$ | H | p-COOH phenyl |
| 32 | S—CH$_3$ | H | OCH$_3$ | H | p-COOH phenyl |
| 33 | S—CH$_3$ | OCH$_3$ | H | H | p-COOCH$_3$ phenyl |
| 34 | R—CH$_3$ | OCH$_3$ | H | H | p-COOCH$_3$ phenyl |
| 35 | CH$_3$ | H | —O—CH$_2$—O— | | ![HOOC-phenyl] |
| 36 | CH$_3$ | H | —O—CH$_2$—O— | | p-OHphenyl |
| 37 | H | H | —O—CH$_2$—O— | | p-OHphenyl |
| 38 | H | H | —O—CH$_2$—O— | | 3-F,4-OH-phenyl |
| 39 | H | H | —O—CH$_2$—O— | | 3,5-di-F,4-OH-phenyl |
| 40 | H | H | —O—CH$_2$—O— | | 3,5-di-F,4-OCH$_3$-phenyl |
| 41 | S—CH3 | H | —O—CH$_2$—O— | | p-COOH-phenyl |
| 42 | R—CH$_3$ | H | —O—CH$_2$—O— | | p-COOH-phenyl |
| 43 | CH$_3$ | H | —O—CH$_2$—O— | | 2,3,5-tri-F,4-OH-phenyl |
| 44 | CH$_3$ | H | —O—CH$_2$—O— | | 2,3,5,6-tetra-F,4-OH-phenyl |
| 45 | CH$_3$ | H | —O—CH$_2$—O— | | 3-CN, 4-OH-phenyl |
| 46 | CH$_3$ | H | —O—CH$_2$—O— | | 4-CH$_3$SO$_2$HN-phenyl |
| 47 | CH$_3$ | H | —O—CH$_2$—O— | | 4-CH$_3$HNSO$_2$-phenyl |

TABLE 1-continued

| Cpd | A | V | W | M | Ar |
|---|---|---|---|---|---|
| 48 | $CH_3$ | H | | —O—$CH_2$—O— | 5-(2-HOOC-pyridyl) |
| 49 | $CH_3$ | H | | —O—$CH_2$—O— | 4-(HO-NH-C(O)-)phenyl |
| 50 | $CH_3$ | H | | —O—$CH_2$—O— | 3,4,-di-OH-phenyl |
| 51 | $CH_3$ | H | | —O—$CH_2$—O— | N-(4-oxo-pyridyl) |
| 52 | H | H | OMe | H | 4-(HOOC-$CH_2$-)phenyl |
| 53 | H | H | OMe | H | 4-($H_2N$-CH(COOH)-)phenyl |
| 54 | $CH_3$ | H | | —O—$CH_2$—O— | N-methyl-imidazol-5-yl |
| 55 | R—$CH_3$ | H | | —O—$CH_2$—O— | pyrid-4-yl |
| 56 | H | $OCH_3$ | H | H | N-methyl-imidazol-5-yl |
| 57 | R—$CH_3$ | $OCH_3$ | H | H | pyrid-4-yl |
| 58 | R—$CH_3$ | H | $OCH_3$ | H | p-COOH phenyl |
| 59 | H | H | $OCH_3$ | H | p-COOH phenyl |
| 60 | H | H | $OCH_3$ | $OCH_3$ | 4-Pyridyl |

Pharmaceutical Compositions

The disclosure includes a pharmaceutical composition containing at least one compound of formula I as the active agent together with a pharmaceutically acceptable carrier.

The pharmaceutical compositions of the disclosure include ocular, oral, nasal, transdermal, topical with or without occlusion, intravenous (both bolus and infusion), inhalable, and injection (intraperitoneally, subcutaneously, intramuscularly or parenterally) formulations. The composition may be in a dosage unit such as a tablet, pill, capsule, powder, granule, liposome, sterile ocular solution, parenteral solution or suspension, metered aerosol or liquid spray, drop, ampoule, auto-injector device, or suppository; for administration ocularly, orally, intranasally, sublingually, parenterally, or rectally, or by inhalation or insufflation.

The dosage form containing the composition of the disclosure contains an effective amount of the active agent necessary to provide a therapeutic effect by the chosen route of administration. The composition may contain from about 5,000 mg to about 0.5 mg (preferably, from about 1,000 mg to about 0.5 mg) of a compound of the disclosure or salt form thereof and may be constituted into any form suitable for the selected mode of administration. The dosage form may be formulated for immediate release or controlled release, including delayed release or sustained release. The pharmaceutical composition may include a compound for formula I as the only active agent or may be combined with one or more additional active agents. In certain embodiments the pharmaceutical composition includes a compound of formula I and at least one direct acting antibiotic (a compound efficacious for killing pathogenic bacteria in vivo).

Methods of Treatment

The disclosure includes a method of treating a bacterial infection in a subject by administering an effective amount of one or more compounds of the disclosure to a subject at risk for a bacterial infection or suffering from a bacterial infection. The disclosure includes a method of treatment in which a compound of formula I is used to treat a bacterial infection and methods in which a compound is used to sensitize bacteria to an antibacterial agent. In this embodiment a compound of formula I is administered to a patient having a bacterial infection, simultaneously or sequentially, with a therapeutically effective amount of the antibacterial agent. The compound of formula I increases the efficacy, often by lowering the MIC, of the other antibacterial agent.

Treatment of human patients is particularly contemplated. However, treatment of non-human subjects is within the scope of the disclosure. The disclosure includes treatment or prevention of microbial infections in fish, amphibians, reptiles or birds, but a preferred embodiment of the disclosure includes treating mammals.

In some embodiments, the bacterial infection or antibiotic-tolerant or antibiotic-resistant infection is caused by a Gram-positive bacterium.

In other embodiments, the bacterial infection or antibiotic-tolerant or antibiotic-resistant infection is caused by a Gram-negative bacterium.

In some embodiments, the bacterial infection is a *Mycobacterium tuberculosis* (Mtb). In some embodiments the *Mycobacterium tuberculosis* infection is a strain that is multi-drug resistant, for example a strain resistant to amikacin, kanamycin, and/or capreomycin. Certain compounds disclosed herein inhibit Mtb with MIC values less than 1 g/mL.

In an embodiment of any of the methods of this disclosure, the microbial infection is the result of a pathogenic bacterial infection. Examples of pathogenic bacteria include, without limitation, bacteria within the genera *Aerobacter, Aeromonas, Acinetobacter, Agrobacterium, Bacillus, Bacteroides, Bartonella, Bordetella, Brucella, Burkholderia, Calymmatobacterium, Campylobacter, Citrobacter, Clostridium, Corynebacterium, Enterobacter, Enterococcus, Escherichia, Francisella, Haemophilus, Hafnia, Helicobacter, Klebsiella, Legionella, Listeria, Morganella, Moraxella, Proteus, Providencia, Pseudomonas, Salmonella, Serratia, Shigella, Staphylococcus, Streptococcus, Treponema, Xanthomonas, Vibrio*, and *Yersinia*. Specific examples of such bacteria include *Vibrio harveyi, Vibrio cholerae, Vibrio parahemolyticus, Vibrio alginolyticus, Pseudomonas phosphoreum, Pseudomonas aeruginosa, Yersinia enterocolitica, Escherichia coli, Salmonella typhimurium, Haemophilus influenzae, Helicobacter pylori, Bacillus subtilis, Borrelia burgdorferi, Neisseria meningitidis, Neisseria gonorrhoeae, Yersinia pestis, Campylobacter jejuni, Mycobacterium tuberculosis, Enterococcus faecalis, Streptococcus pneumoniae, Streptococcus pyogenes, Klebsiella pneumoniae, Burkholderia cepacia, Acinetobacter baumannii, Staphylococcus epidermidis*, and *Staphylococcus aureus*.

In some embodiments the infection is a yeast infection, such as *Candida albicans*.

In some embodiments, the infection is a polymicrobial infection, e.g., an infection comprising more than one organism. In some embodiments, the infection comprises at least one of the organisms listed above, e.g., one or more of *Pseudomonas*, e.g., *P. aeruginosa, Klebsiella*, e.g., *Klebsiella pneumoniae*, and/or *Acinetobacter*, e.g., *A. baumannii*.

In some embodiments, the methods further include administering an additional active agent in combination with a compound of the disclosure, such as an antibiotic selected from the group consisting of but not limited to: beta-lactams such as penicillins, cephalosporins, carbacephems, cephamycins, carbapenems, monobactams, quinolones including fluoroquinolones and similar DNA synthesis inhibitors, tetracyclines, aminoglycosides, macrolides, glycopeptides, chloramphenicols, glycylcyclines, lincosamides, lipopeptides, lipodepsipeptides, such as daptomycin, and oxazolidinones.

In some embodiments, the bacterial infection is an upper and lower respiratory tract infection, pneumonia, bacteremia, a systemic infection, sepsis and septic shock, a urinary tract infection, a gastrointestinal infection, endocarditis, a bone infection, central nervous system infections such as meningitis, or an infection of the skin and soft tissue.

In some embodiments, the subject is a mammal, e.g., a human or non-human mammal. In some embodiments, the methods include treating one or more cells, e.g., cells in a culture dish.

In one aspect, the present disclosure features a method of treating a Gram-negative infection in a subject, the method comprising administering to said subject in need of such treatment a therapeutically effective amount of a compound described herein.

In some embodiments, the Gram-negative infection is caused by *Pseudomonas aeruginosa*.

In other embodiments the disclosure includes treating an infection caused by Gram-positive bacteria, such as *Staphylococcus epidermidis* and *Staphylococcus aureus*.

In some embodiments, the subject is a trauma patient or a burn patient suffering from a burn or skin wound.

In a further aspect, the present disclosure features a method of reducing bacterial tolerance in a subject, the method comprising administering to said subject a therapeutically effective amount of a compound described herein.

In some embodiments, the method further includes identifying said subject suffering from an infection with bacteria resistant to antimicrobial therapy.

The disclosure includes methods of treatment in which a compound or composition of the disclosure is administered orally, topically, intravenously, or parenterally, or is inhaled.

A compound of the disclosure may be administered about 1 to about 5 times per day. Daily administration or post-periodic dosing may be employed. Frequency of dosage may also vary depending on the compound used, the particular disease treated and the bacteria causing the disease. It will be understood, however, that the specific dose level for any particular subject will depend upon a variety of factors including the activity of the specific compound employed, the age, body weight, general health, sex, diet, time of administration, route of administration, and rate of excretion, drug combination and the severity of the particular disease undergoing therapy.

Anti-Tuberculosis Effects of PLA DHFR Inhibitors

Inventors have established DHFR inhibition as a mechanism for cell growth inhibition. Certain compounds of the disclosure were also tested for antibacterial activity in two *M. smegmatis* strains that overexpress DHFR under the control of two different promoters. All compounds, with the exception of UCP 1066, have significantly increased MIC values of at least 32 µg/mL in both strains, indicating that the antibacterial activity is likely due to DHFR inhibition. This compound has an MIC value of 4 µg/mL in the overexpressing strains, which is the same as its value against the Erdmann strain.

Inventors expressed and purified *M. tuberculosis* DHFR (MtbDHFR) protein and measured enzyme inhibition (See Table 6, Example 10) using standard procedures that spectroscopically follow the oxidation of the cofactor NADPH at 340 nm. Experiments were performed in triplicate and verified on two different dates. Many of the inhibitors tested in the assay are moderately potent against the MtbDHFR enzyme with $IC_{50}$ values in the range 70-600 nM. The range of $IC_{50}$ values is relatively narrower than the range of MIC values, again suggesting that activity against the enzyme is only one of the factors that drives antibacterial potency. Table 6 shows that most of the compounds have very similar $IC_{50}$ values against the human enzyme. In order to investigate potential human cell toxicity, cytotoxic effects of these potent compounds have been assessed in human dermal fibroblasts, HepG2 and MCF-10 cells. In all cases, the growth of the cells is not inhibited with compound concentrations less than 500 µM.

PLAs of the disclosure have also been assessed: five multi-drug resistant TB strains, Mtb 365, Mtb 276, MTb 352, Mtb 56 and Mtb C-31 and one extensively drug-resistant (XDR) strain, Mtb 5. See Table 7, Example 10. Overall, each of the strains are resistant to INH with MIC values between 0.25-4 µg/mL. Three of the strains, Mtb 5, Mtb 365 and Mtb 56, are also highly resistant to rifampin with MIC values of 8, 64 and 32 µg/mL, respectively. The strains are also resistant to a variety of other agents including ethambutol, streptomycin and moxifloxacin. The PLAs are active against the majority of the MDR strains, albeit at slightly decreased levels. The compounds did not show activity against strain C-31. Excitingly, compounds 58 and 59 are very active against the MDR strain (Mtb 352) and XDR strains (Mtb 5) with MIC values of 0.06 or 0.5 µg/mL, respectively, against Mtb 352 and 0.25 and 2 µg/mL against Mtb 5.

Abbreviations

| | | | |
|---|---|---|---|
| BSA | Bovine Serum Albumin | MeOH | Methanol |
| DCM | Dichloromethane | NADPH | Nicotinamide adenine dinucleotide phosphate |
| DMF | Dimethyl furan | Sa | *Staphylococcus aureus* |
| DMSO | Dimethyl sulfoxide | TES | N-[Tris(hydroxymethyl)methyl]-2-aminoethanesulfonic acid |
| Ec | Escherichia coli | TFA | Trifluoroacetic Acid |
| EDTA | Ethylene Diamine Tetra Acetic acid | THF | Tetrahydrofuran |
| EtOAc | Ethyl Acetate | TLC | Thin Layer Chromotography |
| HRMS | High resolution mass spectroscopy | TMSCl | Trimethyl silyl chloride |
| KOAc | Potassium Acetate | UPLC | Ultra performance liquid chromatography |

EXAMPLES

General Methods

The $^1H$ and $^{13}C$ NMR spectra were recorded on Bruker instruments at 400 MHz. Chemical shifts are reported in ppm and are referenced to residual DMSO solvent; 2.50 and 39.51 ppm for $^1H$ and $^{13}C$ respectively. The high-resolution mass spectrometry was provided by University of Connecticut Mass Spectrometry Laboratory using AccuTOF mass spectrometer with a DART source. Optical rotation was measured on a Jasco P-2000 polarimeter at 589 nm. TLC analyses were performed on Sorbent Technologies silica gel HL TLC plates. All glassware was oven-dried and allowed to cool under an argon atmosphere. Anhydrous dichloromethane, ether, and tetrahydrofuran were used directly from Baker Cycle-Tainers. Anhydrous dimethylformamide was purchased from Acros and degassed by purging with argon. All reagents were used directly from commercial sources unless otherwise stated. A premixed heterogeneous mixture of CuI (10%/w) in $Pd(PPh_3)_2Cl_2$—(Pd/Cu) was used for the Sonogashira coupling.

Example 1. Synthesis of Zwitterionic PLAS

Compounds of the disclosure were prepared by coupling t-butyl benzoates via Suzuki reaction to suitable B-ring benzaldehydes 1 followed by chain extension and Sonagashira coupling with the diaminopyrimidine headgroup. Final deblocking of the t-butyl ester under strong acidic conditions proceeded smoothly and in good yield (Scheme 1).

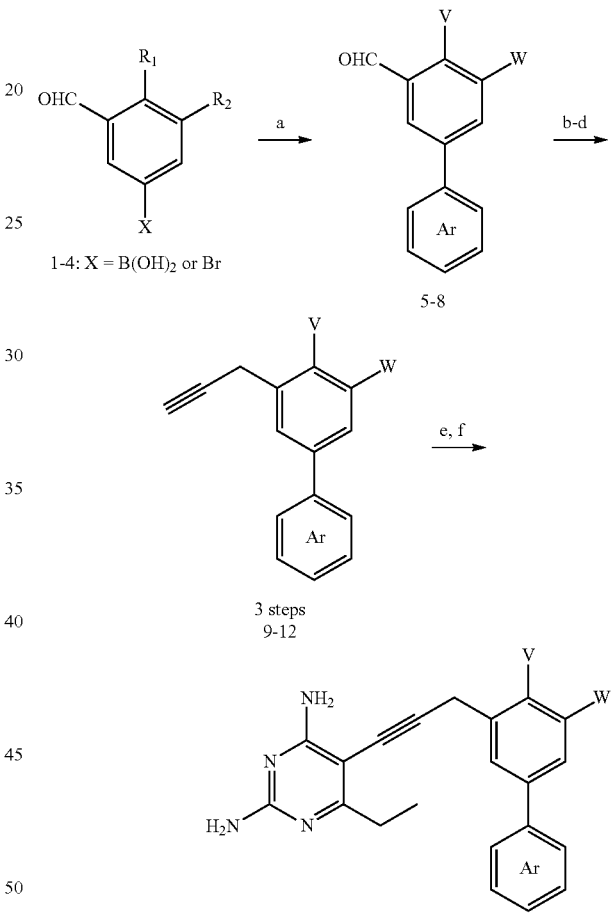

Scheme 1. Zwitterionic PLA synthesis

13: V = OMe, W = H, Ar = o-COOH
14: V = OMe, W = H, Ar = m-COOH
15: V = OMe, W = H, Ar = p-COOH
16: V = H, W = OMe, Ar = p-COOH (a) Ar—$B(OH)_2$ or Ar—Br, $Pd(PPh_3)_4$, $Cs_2CO_3$, Dioxane:$H_2O$, 90 °C;
(b) methoxymethyl triphenylphosphonium chloride, $NaO^tBu$, THF, 0 °C;
(c) NaI, TMSCl, MeCN, -20° C.; (d) dimethyl(1-diazo-2-oxopropyl)phosphonate, $K_2CO_3$, MeOH; (e) Iodoethyl diaminopyrimidine, $Pd(PPh_3)_2Cl_2$, CuI, KOAc, DMF, 50° C.; (f) TFA, DCM.

Example 2. Synthesis of Methyl Branched Homologs

Methyl-branched homologs of 15 and 16 were prepared using known methods. (Viswanathan, K., et al., PloS One (2012) http://dx.doi.org/10.1371/joumrnal.pone.0029434))
Synthesis of PLA enantiomers began from the previously reported asymmetric thioesters (17-20) that were coupled to 4-methylbenzoate boronic acid via Suzuki coupling. Similar to the racemic synthesis, methyl ester cleavage could be achieved as the last synthetic step, affording compounds 29-34.

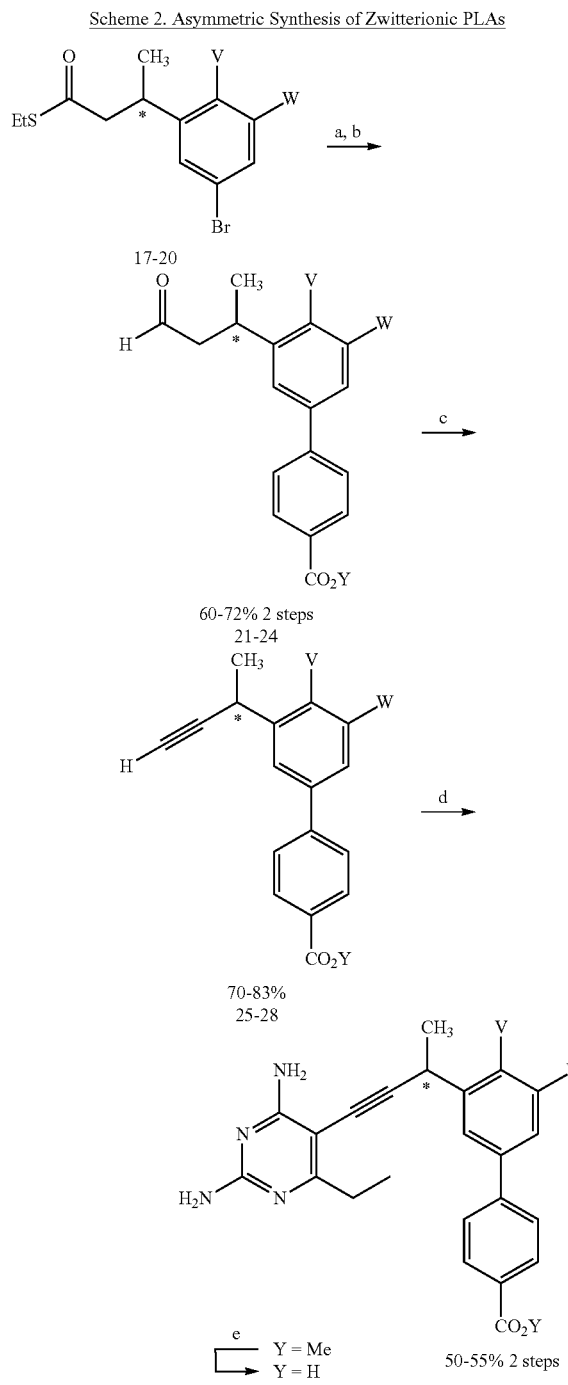

29(S), 30(R): V=OMe, W=H, Y=H
31(R), 32(S): V=H, W=OMe, Y=H (a) PdCl₂(PPh₃)₂, 4-Methoxycarbonylphenylboronic acid, Dioxane: H₂O, 90° C.;
(b) 10% Pd/C, Et₃SiH, DCM; (c) Nonaflyl flouride, P₁-t-Bu-tris(tetramethylene) phosphazene base, DMF, -15° C. to rt; (d) Iodoethyl diaminopyrimidine, Pd(PPh₃)₂, CuI, KOAc, DMF, 50° C; (e) LiOH, THF:H₂O, 32° C.

Example 3. Synthesis of (S)-4-(6-(4-(2,4-diamino-6-ethylpyrimidin-5-yl)but-3-yn-2-yl)benzo[d][1,3]dioxol-4-yl)benzoic acid: (Compound 41)

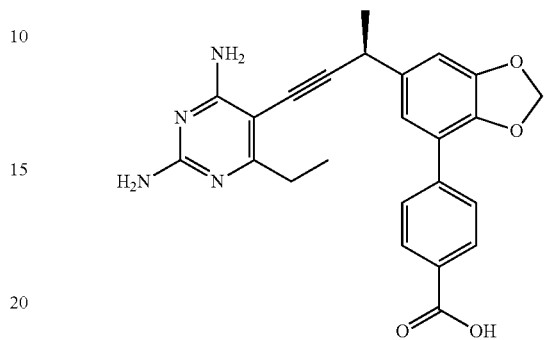

To a 20 mL screw cap vial with stirbar was added (0.57 mmol, 0.15 g, 1eq) ethyl-iododiaminopyrimidine, (0.05 mmol, 0.03 g, 0.08 eq) Pd/Cu and (5.7 mmol, 0.55 g, 10 eq) KOAc. Argon purged anhydrous DMF (0.05M, 11.3 mL) was added followed by alkyne (0.73 mmol, 0.25 g, 1.3 eq). The reaction mixture was stirred under argon for 15 min and degassed once using freeze/pump/thaw method. The vial was sealed under argon, heated at 60° C. and reaction monitored by TLC. At the end of the reaction, the dark reddish brown solution was concentrated and product purified by flash column chromatography (for preabsorption of crude mixture —SiO₂ in 10%/w of cysteine—1.5 g, NH₂ capped SiO₂—1.5 g), 13 g SiO₂ for column, 2% MeOH/CH₂Cl₂) to afford the coupled pyrimidine as pale brown solid. (0.2 g, 72% yield). TLC $R_f$=0.4 (5% MeOH/CH₂Cl₂). The pyrimidine coupled t-butyl ester product (0.0411 mmol, 0.02 g, 1eq) in (0.02M, 2 mL) d-CHCl₃ cooled to 0° C. was deprotected using trifluoroacetic acid (TFA) (8.22 mmol, 200 eq, 0.63 mL). After dropwise addition, the reaction mixture was brought to room temperature. At the end of the reaction, monitored by NMR, the reaction mixture was rotoevaporated at 20° C., kept under vacuum for 15 mins to remove excess TFA. To the product mixture containing a small amount of TFA was added anhydrous CH₂Cl₂ for preabsorption onto silica gel (1g). Flash column chromatography was performed (5 g silica gel) initially with 100% EtOAc followed by 0.01% TFA in EtOAc; TLC $R_f$=0.3 (10% MeOH/CH₂Cl₂ with 0.01% TFA). The clean fractions were rotoevaporated at 20° C. ensuring complete removal of solvent. The oily TFA salt was neutralized with phosphate buffer at pH 7. The resulting white precipitate along with buffer solution was transferred to an Eppendorf tube and centrifuged to separate the water from the precipitate. After decanting the water layer, the white precipitate was rinsed with diethyl ether and methanol to remove the water. The dried white solids with a tinge of pink color (0.01 g, 57% yield) were subjected to characterization and biological evaluation. ¹H NMR (400 MHz, DMSO-d) δ 8.03 (d, J=8.4

Hz, 2H), 7.86 (d, J=8.4 Hz, 2H), 7.28 (s, 1H), 7.09 (s, 1H), 6.28 (broad, 2H), 6.18 (s, 2H), 6.12 (s, 2H), 4.12 (q, J=7 Hz, 1H), 2.55 (q, J=7.6 Hz, 2H), 1.54 (d, J=7.1 Hz, 3H), 1.11 (t, J=7.6 Hz, 3H); $^{13}$C NMR (100 MHz, DMSO-d) 6171.5, 167.1, 164.2, 161.1, 148.1, 143.4, 139.5, 138.4, 129.8, 129.7, 127.5, 120.2, 118.8, 107.3, 101.2, 100.5, 87.8, 76.0, 32.0, 28.8, 24.6, 12.4; HRMS (DART, M++H) m/z 431.1708 (calculated for $C_{24}H_{23}N_4O_4$, 431.1719); $[\alpha]^{24}$+3.3° (c, 0.146, DMSO).

Example 4. Synthesis of (R)-4-(6-(4-(2,4-diamino-6-ethylpyrimidin-5-yl)but-3-yn-2-yl)benzo[D][1,3]dioxol-4-yl)benzoic acid

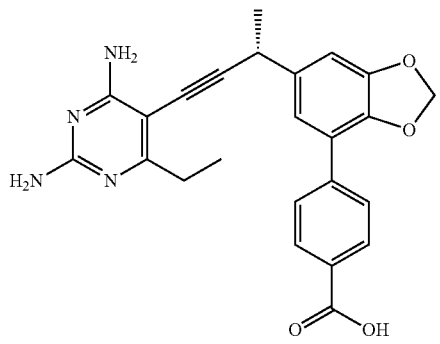 [SMILES: CCc1nc(N)nc(N)c1C#C[C@H](C)c1cc2c(c(-c3ccc(C(=O)O)cc3)c1)OCO2]

To a 20 mL screw cap vial with stirbar was added (0.45 mmol, 0.12 g, 1eq) ethyl-iododiaminopyrimidine, (0.04 mmol, 0.025 g, 0.08 eq) Pd/Cu and (4.47 mmol, 0.44 g, 10 eq) KOAc. Argon purged anhydrous DMF (0.05M, 8.9 mL) was added followed by alkyne (0.58 mmol, 0.20 g, 1.3 eq). Following the same workup as the (S) enantiomer, (R) enantiomer was obtained as a pale brown solid (0.164 g, 75% yield). TLC $R_f$=0.4 (5% MeOH/$CH_2Cl_2$); The pyrimidine coupled t-butyl ester product (0.062 mmol, 0.03 g, 1eq) in (0.02M, 3 mL) d-$CHCl_3$ cooled to 0° C. was deprotected using trifluoroacetic acid (TFA) (18.50 mmol, 300 eq, 1.42 mL). Repeating the same deprotection workup as above, (R) carboxylic acid was obtained as a white solid with a tinge of pink color (0.015 g, 56% yield). TLC $R_f$=0.3 (10% MeOH/$CH_2Cl_2$ with 0.01% TFA); $^1$H NMR (400 MHz, DMSO-d) δ 8.03 (d, J=7.6 Hz, 2H), 7.87 (d, J=7.2 Hz, 2H), 7.27 (s, 1H), 7.09 (s, 1H), 6.26 (broad, 2H), 6.15 (s, 2H), 6.12 (s, 2H), 4.11 (q, J=7 Hz, 1H), 2.56 (m, 2H), 1.53 (d, J=7.0 Hz, 3H), 1.11 (t, J=7.5 Hz, 3H); $^{13}$C NMR (100 MHz, DMSO-d) 6171.6, 167.0, 164.2, 161.1, 148.1, 143.4, 139.5, 138.4, 129.8, 129.7, 127.5, 120.2, 118.8, 107.3, 101.2, 100.5, 87.8, 76.0, 32.0, 28.8, 24.6, 12.4; HRMS (DART, M++H) m/z 431.1708 (calculated for $C_{24}H_{23}N_4O_4$, 431.1719); $[\alpha]^{24}$-5.2° (c, 0.143, DMSO).

Example 5. DHFR Inhibition Assays

Recombinant SaDHFR and EcDHFRin PET-41a(+) were over-expressed in E. coli BL21 (DE3) (Invitrogen) cells and purified using nickel affinity chromatography (5 Prime). Protein was desalted using a PD-10 column (GE Healthcare) into buffer containing 20 mM Tris pH 7.0, 20% glycerol, 0.1 mM EDTA, 2 mM DTT and stored in aliquots at -80° C.
S. aureus MICs Minimum inhibitory concentrations were determined according to Clinical and Laboratory Standards Institute's guideline for Standard Micro-dilution broth assay using a final inoculum of $5 \times 10^5$ CFU/mL of ATCC strain 43300 in Isosensitest Broth (Oxoid). The MIC was defined as the lowest concentration of inhibitor to visually inhibit growth. Growth was monitored at $A_{600}$ after 18 h of incubation at 37° C. MICs were confirmed, colorimetrically, using Presto Blue (Life Technologies). E. coli Minimum inhibitory concentrations were determined using E. coli (ATCC 25922) and the microdilution broth assay with an inoculum of $1 \times 10$ CFU/mL in Isosensitest Broth (Oxoid). Growth was monitored at $A_{600}$ using the Alamar Blue assay; the MIC is defined as the lowest concentration of inhibitor to completely inhibit growth.

Compounds 13-16 and 29-34 were evaluated for their inhibition ($IC_{50}$ values) of the S. aureus (Sa), E. coli (Ec) and human (Hu) DHFR enzymes and data is shown in Table 1. $IC_{50}$ values for both Sa and EcDHFR enzymes were determined using enzyme inhibition assays by monitoring the rate of NADPH oxidation by DHFR via absorbance at 340 nM. The reaction was performed at room temperature in buffer containing 20 mM TES pH 7.0, 50 mM KCl, 0.5 mM EDTA, 10 mM ME and 1 mg/mL BSA, 0.1 mM NADPH and 2 μg/mL enzyme. Inhibitor in DMSO was added to the enzyme/NADPH mixture and incubated for 5 minutes prior to the addition of 0.1 mM dihydrofolate in 50 mM TES. The number provided in parenthesis in the SaDHFR and EcDHFR $IC_{50}$ columns represents the fold selectivity over inhibition of the human DHFR enzyme.

Compound inhibition of S. aureus (Sa), E. coli (Ec) and human (Hu) DHFR enzymes (TABLES 2 and 3) is shown.

TABLE 2

Zwitterionic PLA Compounds and Biological Activity

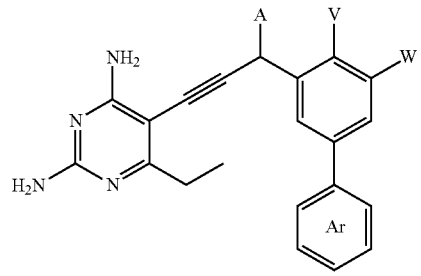

| Cpd | A | V | W | Ar = Phenyl, sub. with | Sa $IC_{50}$ (μM) | Ec $IC_{50}$ (μM) | Hu $IC_{50}$ (μM) | S. aureus 43300 (μg/mL) | E. coli 25922 (μg/mL) | E. coli NR698 (μg/mL) |
|---|---|---|---|---|---|---|---|---|---|---|
| 13 | H | $OCH_3$ | H | o-COOH | 0.359 (10) | 0.195 (17.9) | 3.5 | >20 | >32 | 20 |

TABLE 2-continued

Zwitterionic PLA Compounds and Biological Activity

| Cpd | A | V | W | Ar = Phenyl, sub. with | Sa IC$_{50}$ (µM) | Ec IC$_{50}$ (µM) | Hu IC$_{50}$ (µM) | S. aureus 43300 (µg/mL) | E. coli 25922 (µg/mL) | E. coli NR698 (µg/mL) |
|---|---|---|---|---|---|---|---|---|---|---|
| 14 | H | OCH$_3$ | H | m-COOH | 0.157 (9.5) | 0.526 (3.4) | 1.5 | 0.625 | >20 | 0.0391 |
| 15 | H | OCH$_3$ | H | p-COOH | 0.032 (25) | 0.090 (9) | 0.817 | 0.0195 | >20 | 0.0098 |
| 16 | H | H | OCH$_3$ | p-COOH | 0.011 (63) | 0.507 (1.35) | 0.688 | 0.0195 | >20 | 0.0049 |
| 29 | S—CH$_3$ | OCH$_3$ | H | p-COOH | 0.037 (7.2) | 0.177 (1.5) | 0.266 | 0.625 | >20 | 0.0391 |
| 30 | R—CH$_3$ | OCH$_3$ | H | p-COOH | 0.216 (2.4) | 0.289 (1.8) | 0.52 | 0.0195 | 20 | 0.0012 |
| 31 | R—CH$_3$ | H | OCH$_3$ | p-COOH | 0.009 (28) | 0.084 (3) | 0.254 | 0.0098 | 10 | 0.0024 |
| 32 | S—CH$_3$ | H | OCH$_3$ | p-COOH | 0.014 (36) | 0.166 (3) | 0.502 | 0.0098 | 10 | 0.0024 |
| 33 | S—CH$_3$ | OCH$_3$ | H | p-COOCH$_3$ | 0.022 | 0.034 | | 0.625 | >20* | 0.156 |
| 34 | R—CH$_3$ | OCH$_3$ | H | p-COOCH$_3$ | 0.205 | 0.172 | | 10 | >20* | 1.875 |

TABLE 3

Additional Zwitterionic PLA Structure and Biological Activity

| Cpd | A | Ar = Phenyl, sub. with | Sa IC$_{50}$ (µM) | Ec IC$_{50}$ (µM) | Hu IC$_{50}$ (µM) | S. aureus 43300 (µg/mL) | E. coli 25922 (µg/mL) | E. coli NR698 (µg/mL) |
|---|---|---|---|---|---|---|---|---|
| 35 | CH$_3$ | p-CH$_2$—C(O)—OH | | | | | | |
| 36 | CH$_3$ | p-OH | | | | | | |
| 37 | H | p-OH | 2.5 | | | 0.625 | | 0.002 |
| 38 | H | 3-F,4-OH | 1.25 | | | 0.625 | | 0.001 |
| 39 | H | 3,5-di-F, OH | 0.625 | | | 0.625 | | 0.001 |
| 40 | H | 3,5-di-F, OCH$_3$ | >20 | | | 5 | | 0.78 |

Example 6. Structural Studies

Structures of SaDHFR bound to the zwitterionic compounds 15 and 16 were determined by X-ray crystallography.

SaDHFR:NADPH:15

Purified SaDHFR at 18 mg/mL protein was co-crystallized with 2 mM NADPH and 1 mM inhibitor 15 in DMSO via the hanging drop method. The mixture of protein and cofactor was incubated on ice for 3 hours. Equal volumes of protein solution were added to an optimized buffer solution containing 0.1 M MES, pH 5.5, 0.2 M sodium acetate, 17% PEG 10,000 and 12.5% gamma-butyrlactone. When stored at 4° C., crystals typically formed within 7 days. Crystals were harvested and frozen in cryo-protectant buffer containing 25% glycerol. Data were collected remotely on beamline 7-1 at Stanford Synchrotron Radiation Lightsource, SLAC National Accelerator Laboratory. Data were indexed and scaled using HKL2000. Phaser crystallographic software (McCoy, A. J. et al., J. Appl. Cryst., (2007) 40:658-674) was used to identify molecular replacement solutions using PDB ID: 3F0Q as a probe. Coot and Phenix were used for structure refinement until acceptable RWork and RFree were achieved.

SaDHFR:NADPH:16

Purified SaDHFR was co-crystallized with 2 mM NADPH and 1 mM 16 in DMSO via hanging drop method. Crystallization details were similar to those used above except for a change in buffer to 0.1M MES, pH 5.0. Data were collected on the Rigaku Highflux Homelab system at the University of Connecticut's Protein X-Ray Crystallography Facility. Data were indexed and scaled using Structure Studio (d*Trek). Similar to above, Phaser was used for molecular replacement; Coot (Emsley, P. and Cowtan, K., Acta Crysta., (2004) D50: 2126-2132) and Phenix (Adams, P. D., Acta Cryst., (2010) D66: 213-221) were used for structure refinement.

Figure 2D:
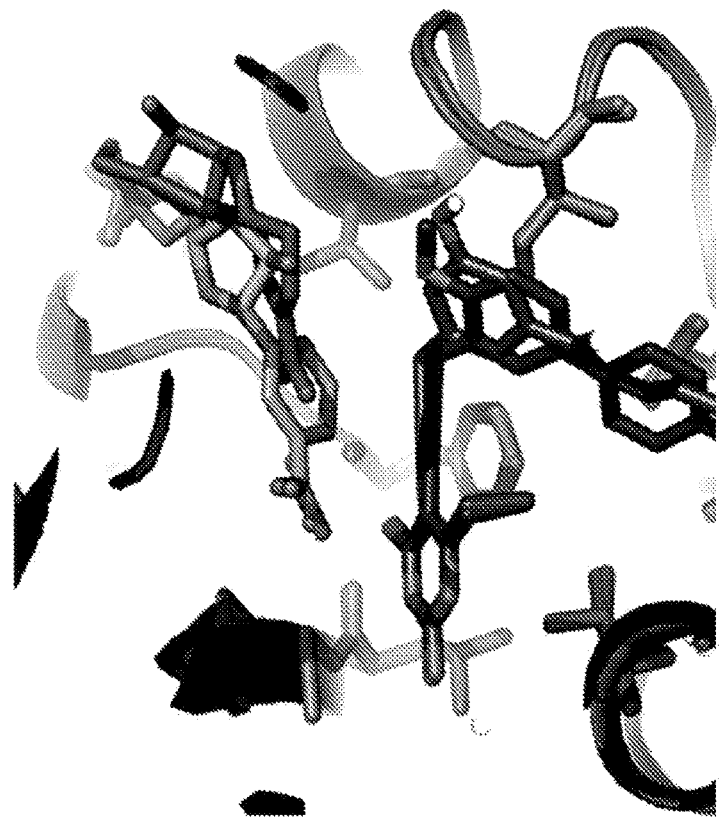
FIG. 2D, solvent exposed surface of complex S. aureus DHFR bound to compound 16.
Figure 2C:
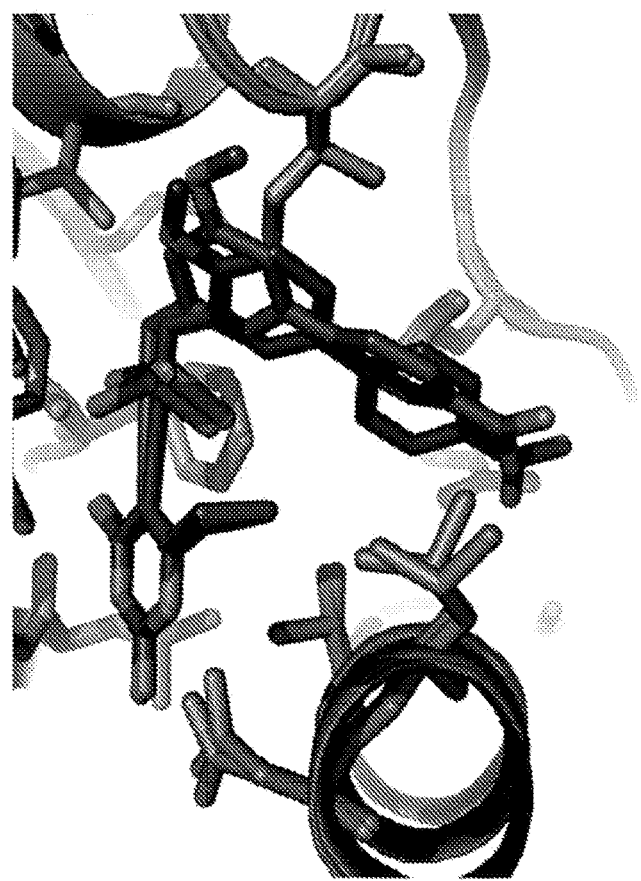
FIG. 2. Diagram of S. aureus DHFR crystallized with NADPH and either compound 15 or compound 16.
FIG. 2A, S. aureus DHFR bound to compound 15.
FIG. 2B, S. aureus DHFR bound to compound 16; 2C, solvent exposed surface of complex S. aureus DHFR bound to compound 15.

Crystals of SaDHFR complexed with NADPH and inhibitor 15 or 16 produced diffraction amplitudes to 2.24 Å or 1.81 Å, respectively. The structures were solved using molecular replacement methods based on PDB 3F0Q (Frey, K. M. et al., J. Structural Biology (2010) 170(1): 93-97) as a model. Both structures feature the bound antifolate and either dual occupancy of β-NADPH and its alternative α-anomer (the structure with compound 15 shows the α-anomer in a ring-closed tautomer state (Fox, K. M. and Karplus, P. A., Structure (1994) 2(11): 1089-1105) or full occupancy of the α-anomer (structure with compound 16). The structure bound to compound 15 shows the coordination of a water molecule between the carboxylic acid and the side chain of Arg 57 (FIG. 2A). The structure with compound 16 (FIG. 2B) exhibits an extensive water network involving at least four water molecules, coordinated between the carboxylic acid of 16, both amino groups on Arg 57 as well as the carbonyl oxygen of Leu 28. The water network expands to include additional hydrogen bonding interactions with the side chains of Asn 56 and Thr 36 (FIG. 2B). The binding modes of the inhibitor represent significant differences in the crystal structures with inhibitors 15 and 16. The methoxy substitution in the $R_1$ position of compound 15 shifts the biaryl system 1.2 Å toward the solvent exposed surface, which is likely responsible for differences in the observed water networks between compounds 15 and 16 (FIG. 2C).

Both structures feature the α-anomer of NADPH in the cofactor binding site. The structure with SaDHFR:NADPH:15 shows 40% occupancy and that with SaDHFR:NADPH:16 shows 100% occupancy. The α-anomer displaces a water molecule coordinated between the nicotinamide phosphate of β-NADPH and the sidechain of Asn 18 that becomes occupied by the cyclized ribose moiety of α-NADPH. In the α-NADPH structures, three water molecules are coordinated between the nicotinamide amide and the backbone of Phe 92, Ile 14 and Ala 7.

X-ray crystallographic determinations and data collections and refinement statistics for crystals of SaDHFR with NADPH and compound 15 or NADPH and compound 16 are provided in Table 4.

TABLE 4

| PDB ID | Sa(WT): NADPH: 15- | Sa(WT): NADPH: 16 |
|---|---|---|
| Space group | $P6_122$ | $P6_122$ |
| No. monomers in asymmetric unit | 1 | 1 |
| Unit cell (a, b, c in Å) | 79.09, 79.09, 107.93 | 79.02, 79.02, 108.25 |
|  | 90.0, 90.0, 120.0 | 90.0, 90.0, 120.0 |
| Resolution (Å) | 32.65-2.24 (2.28-2.24) | 25.15-1.81 (1.87-1.81) |
| Completeness % (last shell, %) | 100 (99.9) | 99.8 (100) |
| Unique reflections | 10,059 | 18,798 |
| Redundancy (last shell) | 14 (14.2) | 12.32 (12.03) |
| Rsym, (last shell) | 0.055 (0.144) | 0.110 (0.644) |
| <I/σ> (last shell) | 68.5 (31.9) | 11.7 (2.3) |
| R-factor/Rfree | 0.2167, 0.1703 | 0.2322/0.1991 |
| No. of atoms (protein, ligands, solvent) | 1,499 | 1,489 |
| Rms deviation bond lengths (Å), angles (deg) | 0.008, 1.912 | 0.009. 1.810 |
| Average B factor for protein (Å2) | 22.34 | 28.01 |
| Average B factor for ligand (Å2) | 17.46 aNADPH | 24.65 NADPH |
|  | 16.91 bNADPH | 24.93 Inhibitor |
|  | 31.29 Inhibitor |  |
| Average B factor for solvent molecules (Å2) | 25.25 | 35.10 |
| Residues in most favored regions (%)[a] | 96.86 | 98.73 |
| Residues in additional allowed regions (%)[a] | 3.14 | 1.27 |
| Residues in disallowed regions (%)[a] | 0.00 | 0 |
| Collection Location | SSRL Beamline 7-1 | Rigaku HighFlux-007 |

Example 7. Cellular Activity of COOH-PLAS p-COOH PLAs exhibit high levels of activity against the SaDHFR enzyme as well as against *S. aureus* with the majority of MIC values ranging from 0.0098-0.625 (Table 1). The compounds displayed reduced activity against wild-type *E. coli*, with compounds 31 and 32 exhibiting MIC values of 10 µg/mL. Two of the major barriers to activity against Gram-negative bacteria are permeability through the outer membrane and active removal of the inhibitor via efflux. To probe permeability as a means of intrinsic resistance, MIC values were measured against NR698, an engineered strain containing an in-frame deletion in the imp gene, which encodes a protein essential for outer membrane assembly}. Inhibition concentrations against the NR698 strain with compounds 15, 16, and 29-32 showed an approximately 2,000-4,000 fold decrease, indicating that reduced penetration through the outer membrane is limiting PLA activity in *E. coli*.

In order to examine whether the COOH-PLAs are subject to efflux by the common AcrB efflux pump, we compared MIC values in a parent *E. coli* strain with those in a strain in which AcrB is deleted (JW0451). As the MIC values against the JW0451 strain are similar to the parent strain and not the NR698 strain (Table 5), it is likely that the compounds are not subject to efflux by AcrB.

TABLE 5

| Compound | E. coli BW25113 | JW0451 |
|---|---|---|
| 13 | >32 | >32 |
| 14 | >20 | >20 |
| 15 | >20 | >20 |
| 16 | >20 | >20 |
| 29 | >20 | >20 |
| 30 | 20 | 20 |
| 31 | 10 | 5 |
| 32 | 10 | 10 |
| 33 | >20* | 2.5* |
| 34 | >20* | 20* |

AcrB, is unlikely as MIC values were also not shifted in ΔacrB, ΔmacB, ΔemrB, or ΔacrF strains further establishing that efflux activity against the major pump AcrB is unlikely

Example 8. Effect of Disclosed Compounds on Human Cells COOH-PLAs have Excellent Drug-Like Properties To examine the drug-like potential of the COOH-PLA compounds of the disclosure, a series of in vitro assays probed their effects on human cells, their inhibition of critical CYP isoforms and their lifetime in microsomal stability assays. The COOH-PLAs have no measurable cytotoxicity ($IC_{50}$>500 µM) toward HepG2 and MCF-10 and cells. Coupling the potent activity against Gram-positive bacterial cells with low cytotoxicity yields a high therapeutic index (>500,000).

Example 9. Effect of Disclosed Compounds on CYP Enzymes

Applicants have also measured cytochrome P450 inhibition for certain compounds of the disclosure. The activity of compound 15 against CYP3A4 and CYP2D6, two of the most prevalent isoforms, was determined. Inhibition of both enzymes requires concentrations greater than 50 µM, indicating the compound can be predicted not to interfere with metabolism of other co-administered therapeutic agents.

Example 10. Microsomal Stability

The lifetime of compound 15 in microsomal stability assays was determined. Compound half-life was measured by following the parent compound using UPLC. The phase I half-life is 99 min. and that for phase II is approximately 87 min. The results of these in vitro experiments point toward an excellent drug-like profile for the COOH-PLAs.

Example 11. Inhibitory Effect of Compounds on *M. Tuberculosis* DHFR and Human DHFR Drugs Isoniazid (INH) was purchased from Sigma Chemical Co., St. Louis, Mo. and dissolved in 100% dimethyl sulfoxide (DMSO) to a concentration of 1 mg/ml prior to freezing at −20° C. The DHFR inhibitors were dissolved in 100% DMSO to a concentration of 20 mg/ml.

Isolates

*M. tuberculosis* ATCC 35801 (strain Erdman) was obtained from the American Type Culture Collection, Manasas, Va. Clinical isolates were obtained from SUNY Upstate Medical University, Syracuse, N.Y. (provided by Betz Forbes), University of Stellenbosch, South Africa (provided by Tommy Victor), National Center of Tuberculosis and Lung Diseases of Georgia, Tbilisi, Georgia (provided by Natalia Shubladze), National Jewish Center, Denver, Colo. (provided by Leonid Heifets).

The mycobacterial isolates were grown in modified Middlebrook 7H10 broth (pH6.6; 7H10 agar formulation with agar and malachite green omitted) supplemented with 10% Middlebrook oleic acid-albumin-dextrose-catalase enrichment (Difco Laboratories, Detroit, Mich.) and 0.05% Tween 80 on a rotary shaker at 37° C. for 5-10 days. The organisms were diluted in 7H10 broth to 1 Klett unit (equivalent to about $5\times10^5$ CFU/ml) using a Photoelectric Colorimeter (Manostat Corp., New York, N.Y.) for use in the broth dilution assay.

Microtiter Broth Dilution MIC Testing

Polystyrene 96-well round-bottom microtiter plates (Corning Inc., Corning, N.Y.) were filled with 50 µl of modified 7H10 broth. The compounds were prepared at 4 times the maximum concentration at which they were to be tested and then were added to the first well prior to being serially diluted 2-fold. INH was tested using a range of concentrations from 8 µg/ml–0.008 µg/ml. The DHFR inhibitors were tested using a range of 32 µg/ml to 0.03 µg/ml. The inocula used for each strain were measured by titration and plated on 7H10 agar plates to determine the actual inocula. The 7H10 agar plates were incubated at 37° C. for 4 weeks. Fifty microliters of the inocula was added to each well containing compound to yield an initial concentration of about $2.5\times10^5$ CFU/ml (range for various isolates tested was $1.25\times10^6$ CFU/ml—$8\times10^4$ CFU/ml). The microtiter plates were covered with SealPlate adhesive sealing film (Exel Scientific, Wrightwood, Calif.) and were incubated at 37° C. in ambient air for 14-21 days prior to reading. Each isolate was tested in duplicate. The MIC was defined as the lowest concentration of antimicrobial agent yielding no visible turbidity.

Expression and Purification of *M. tuberculosis* and Human DHFR

BL21(DE3) competent *E. coli* cells (New England BioLabs) were transformed with recombinant pET-41a(+) plasmid harboring the dfrA gene constructed by GenScript. Transformed cells were grown in LB medium supplemented with 30 µg/mL kanamycin at 37° C. until the $OD_{600}$ reached 0.6-0.7. The cells were induced with 1 mM IPTG for 20 h at 20° C. and spun down at 8000 rpm for 15 minutes. Each gram of wet cell pellet was resuspended in 5 ml of 1× BugBuster reagent (Novagen) supplemented with 200 µg/mL lysozyme and 1 mM DNase I (Thermo Scientific). The cell suspension was incubated for 30 minutes at room temperature with gentle rotation followed by centrifugation at 18,000 rpm for 30 minutes and supernatant was collected. In order to precipitate some of non-target proteins, 40% ammonium sulfate was added to the cell lysate and stirred at 4° C. overnight. After centrifugation at 18,000 rpm for 15 minutes, the supernatant was passed through 0.22 µm filter and slowly loaded onto a methotrexate-agarose column pre-equilibrated with 4 CV of equilibration buffer A (20 mM Tris-HCl, 50 mM KCl, 2 mM DTT, 0.1 mM EDTA and 15% (v/v) glycerol, pH 7.5). The column was washed with 3 CV of wash buffer B (20 mM Tris-HCl, 500 mM KCl, 2 mM DTT, 0.1 M EDTA and 15% (v/v) glycerol, pH 7.5). The enzyme was eluted with 3 CV of elution buffer C (20 mM Tris-HCl, 50 mM KCl, 2 mM DTT, 2 mM DHF, 0.1 mM EDTA and 15% (v/v) glycerol, pH 8.5). Fractions containing DHFR enzyme, were collected, concentrated and loaded onto a Hi-Prep 26/60 Sephacryl s-200 HR column pre-equilibrated with 1 CV of equilibration buffer A (pH 8.5). The protein elution was monitored with AKTA UV/vis diode array spectrophotometer at 280 nm. Fractions containing pure enzyme were pooled, concentrated to 10 mg/ml and flash frozen in liquid nitrogen and stored at −80° C.

Enzyme Inhibition

Enzyme activity and inhibition assays were performed by monitoring the NADPH-dependent reduction of dihydrofolate catalyzed by the DHFR enzyme. The rate of NADPH oxidation was measured spectrophotometrically at 340 nm in assay buffer containing 20 mM TES pH 7.0, 50 mM KCl, 10 mM 2-mercaptoethanol, 0.5 mM EDTA and 1 mg/mL bovine serum albumin. All measurements were performed at room temperature by adding pure enzyme (2 mg/mL), 100 µM NADPH and 100 µM DHF to the buffer. For inhibition assays, inhibitors, dissolved in 100% DMSO, were added to the mixture and incubated for 5 minutes before the addition of DHF. Average $IC_{50}$ values and standard deviations were measured in triplicate.

$IC_{50}$'s for certain PLA compounds at Mtb and human DHFR as well as Mtb MIC's is provided in Table 6. Trimethoprim (TMP), an non-DHFR inhibiting antibiotic was used as a negative control. DHFR inhibitors Isoniazid (INH) and trimetrexate were used as positive controls.

TABLE 6

| Compound | MtbDHFR $IC_{50}$ (nM) | HuDHFR $IC_{50}$ (nM) | MIC (µg/mL) Mtn |
|---|---|---|---|
| 14 | 311 | 1577 | 1 |
| 15 | 173 | 870 | 4 |
| 29 | 111 | 1955 | 0.5 |
| 54 | 326 | 323 | 2 |
| 55 | 206 | 2914 | 4 |
| 56 | 126 | 1452 | 2 |
| 57 | 73 | 144 | 2 |
| 58 | 177 | 1015 | <0.03 |
| 59 | 460 | 688 | 0.5 |
| TMP | 19,560 | 97,179 | 256 |
| Trimetrexate | 17[a] | Nd | 4 |
| INH | — | — | 0.03 |

[a]Data from Nixon, M., et al., Chem. Biol. (2014) 21: 819-30.

Certain compounds of the disclosure were evaluated for antibacterial activity against multidrug-resistant isolates of M. tuberculosis. MIC values for various strains are presented in Table 7.

TABLE 7

| Cmp. | Mtb Erdman | Mtb 5 | Mtb 365 | Mtb 276 | Mtb 352 | Mtb56 | Mtb C-31 |
|---|---|---|---|---|---|---|---|
| 1113 | 8 | 16 | 8 | 16 | 8 | 8 | 16 |
| 15 | 16 | 8 | 4 | 16 | 16 | 16 | >32 |
| 54 | 4 | 8 | 8 | 4 | 4 | 8 | 8 |
| 55 | 8 | 8 | 4 | 8 | 8 | 8 | 16 |
| 56 | 4 | 4 | 4 | 4 | 4 | 4 | 8 |
| 1071 | 8 | 16 | 8 | 16 | 8 | 8 | 32 |
| 1066 | 8 | 16 | 8 | 16 | 16 | 8 | 32 |
| 58 | <0.03 | 0.25 | <0.03 | ND | 0.06 | 0.06 | 8 |
| 59 | 0.5 | 2 | 0.125 | ND | 0.5 | 0.5 | 8 |
| INH | 0.125 | 4 | 2 | ND | 1 | 1 | 4 |

Example 12. Generation and Characterization of MRSA Strains Resistant to Compound A Initial investigations into the potential resistance mechanisms of strain S. aureus 43300 to overcome inhibition by Compound A were previously reported. (Freabxy, K., et al, J. Struct. Biol. (2010) 170: 93-97.)

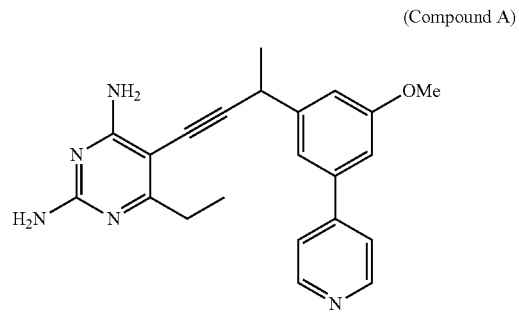 [SMILES: CCc1nc(N)nc(N)c1C#CC(C)c1cc(OC)cc(-c2ccncc2)c1]

(Compound A)

These studies showed that two mutants, F98Y and F98I in the DHFR gene, were selected with low mutation frequencies ($10^{-10}$). To further characterize the resistance profile of the propargyl-linked antifolates, single- and double-step selection studies were carried out and the resulting strains characterized. In single-step studies, mutant selection with the ATCC quality control strain 43300 subjected to compound 1 at 6×MIC yielded three clinically observed mutations: F98Y, H30N and H149R as well as three novel mutations: F151S, F151C and D142Y. A second round of resistance selection using Compound A and progenitor strains possessing F98Y or H149R yielded a series of both novel and clinically relevant double mutants (Table 8). As strains containing H30N/F98Y and F98Y/H149R mutants have been isolated clinically, a full characterization of the fitness of these mutant enzymes and bacteria, including their single mutant counterparts (F98Y, H30N and H149R) at a biochemical, structural and cellular level was performed.

Resistant strains were selected by plating 100 µL of overnight culture (approx. 1012 CFU/mL) of progenitor strain on Isosensitest (Oxoid) agar plates containing 6×MIC of 1 and incubated at 37° C. for 18 hours. Single colonies were isolated and the dfrB gene was identified by directly sequencing the colony PCR product. For colony PCR, cells were lysed using 1 mg/mL lysostaphin and 20 µg/mL proteinase K in 0.1 M Tris, pH 7.5. The gene was amplified using sense primer (5'-ATGACTTTATCCATTCTAGTTGC-3'), anti-sense primer (5'-TTATTTTTTACGAAT-TAAATGTAG-3') and rTaq Polymerase (Takara) following standard PCR conditions. PCR products were purified using Promega Wizard SV Gel and PCR Clean Up system and sequenced using the sense primer.

(Invitrogen) cells with 1 mM IPTG following previously reported procedures. Pellets were lysed using 1× BugBuster (Novagen) and DNase A (ThermoFisher Scientific) and purified using nickel affinity chromatography (SPrime). Protein was desalted using a PD-10 column (GE Healthcare) into buffer containing 20 mM Tris pH 7.0, 20% glycerol, 0.1 mM EDTA, 2 mM DTT and stored in aliquots at −80° C.

TABLE 8

| DHFR Mutation | Progenitor Strain | Single Nucleotide Polymorphism | Colonies Sequenced (%) | Mutational Frequency[a] | Doubling Time (min) |
|---|---|---|---|---|---|
| WT | — | — | — | — | 32.04 |
| F98Y | Sa43300 | TTT to TAT | 2/19 (10.5) | $3.11 \times 10^{-11}$ | 34.53 |
| H30N | Sa43300 | CAT to AAT | 3/19 (15.8) | $4.67 \times 10^{-11}$ | 35.62 |
| H149R | Sa43300 | CAT to CGT | 7/19 (36) | $1.65 \times 10^{-10}$ | 38.34 |
| F98Y/H30N | Sa(F98Y) | CAT to AAT | 2/16 (12.5) | $8.2 \times 10^{-12}$ | 35.06 |
| F98Y/H149R | Sa(H149R) | TTT to TAT | 1/1 (100) | $1.23 \times 10^{-11}$ | 30.89 |

[a]Overall resistance frequency for Sa43300 with Compound A at 6× MIC = 2.96 (±1.58) × $10^{-10}$
Overall resistance frequency for Sa43300(H149R) with Compound A at 6× MIC = 3.75 × $10^{-11}$
Overall resistance frequency for Sa43300(F98Y) with Compound A at 6× MIC = 6.56 (±1.57) × $10^{-11}$ The mutational frequency of 1 was determined by the number of resulting colonies divided by the total inoculum ($1 \times 10^{11}$ CFU/mL) for each progenitor strain. The frequency of the specific mutations was determined by multiplying the mutational frequency for the inhibitor-strain pair by the frequency of sequenced colonies containing the specific mutation.

Minimum Inhibitory Concentrations (MICs)

Minimum inhibitory concentrations were determined according to Clinical and Laboratory Standards Institute's guideline for Standard Micro-dilution broth20 assay using a final inoculum of 5×105 CFU/mL in Isosensitest Broth (Oxoid). The MIC was defined as the lowest concentration of inhibitor to visually inhibit growth. Growth was monitored at $A_{600}$ after 18 h of incubation at 37° C. MICs were confirmed, calorimetrically, using Presto Blue (Life Technologies). Isosensitest broth supplemented with 10 μg/mL thymidine was used to determine any off-target antibacterial activity.

Growth Curves

LB media (50 mL) was inoculated with 1 mL of overnight culture. Growth was monitored at $A_{600}$ every 30 minutes. The doubling time was determined from the linear portion of the growth curve by the following equation:

$$\text{Doubling Time} = \frac{\Delta \text{Time} * \log 2}{\log(\text{Final } Conc.) - \log(\text{Inital } Conc.)}$$

Generation, Expression and Purification of Sa(F98Y, H149R) and Sa(H149R) DHFR Enzymes The generation, expression and purification of Sa(F98Y), Sa(H30N) and Sa(F98Y, H30N) DHFR enzymes have been previously reported[15, 16]. Sa(WT) and Sa(F98Y) in pET-41 a(+) constructs were used for the generation of Sa(H149R) and Sa(F98Y, H149R) DHFR plasmids via QuikChange Lightening Site-Directed Mutagenesis Kit (Stratagene) using sense primer 5'-CTAGATGAGAAAAATACAATTC-CACGTAC-3' and anti-sense primer 5'-CGAAT-TAAATGTAGAAAGGTACGTGGAAT-3' following the manufacturer's instructions. Mutagenesis was confirmed via sequencing. The recombinant Sa (H149R) and Sa (F98Y, H149R) enzymes was over-expressed in *E. coli* BL21 (DE3)

Average overall mutation frequencies for each strain exposed to Compound A were calculated based on the inoculum and number of colonies appearing on multiple plates with a concentration of compound 1 at 6×MIC. Sa43300 exhibits a rise in MIC to Compound A at a very low frequency of $2.96 \times 10^{-10}$. Overall mutation frequencies are even lower to progenitor strains possessing F98Y and H149R, with rates of $6.56 \times 10^{-11}$ and $3.75 \times 10^{-11}$. Specific mutational frequencies were then calculated based on the number of sequenced colonies with a particular mutation. If the generation of double mutants occurs in a step-wise fashion, the combined frequency of resistance could be as low as $10^{-21}$. Evaluation of bacterial fitness, measured by doubling time, shows that the majority of the mutant strains exhibit only minor losses in growth time (1.08-1.2× doubling time of wild-type), with the exception of Sa(F98Y/H149R), which preserved or slightly improved doubling time (Table 8). Overall, these studies show that the mutant strains are relatively fit when compared to wild-type.

The recombinant mutant DHFR enzymes were created by site-directed mutagenesis of the wild-type enzyme and purified using affinity chromatography. Michaelis-Menten kinetics were measured for each enzyme using assay conditions previously published by Frey, et al. (2010) (Table 9). Overall, all enzymes, other than Sa(H149R), have $k_{cat}/K_M$ values within approximately 2-fold of the wild-type value. Sa(H149R) has a significantly reduced $k_{cat}/K_M$ value (6-fold reduction), which is a consequence of higher $K_M$ values for both DHF and NADPH. Interestingly, the double mutant Sa(F98Y/H149R) compensates for the low efficiency of the single Sa(H149R) mutant as the Sa(F98Y/H149R) enzyme restores the $K_M$ value for DHF and NADPH to nearly wild-type values. This compensatory relationship is also observed with the Sa(F98Y/H30N) double mutant. The single H30N mutation suffers a significant decrease in NADPH $K_M$ (31.21 to 79.89 μM); this $K_M$ value is restored to a value near wild-type in the double Sa(H30N/F98Y) mutant.

TABLE 9

Mutant Enzyme Characterization

| DHFR | $K_M$ DHF (μM) | $V_{max}$ DHF | $K_M$ NADPH (μM) | $k_{cat}$ DHF ($s^{-1}$) | $k_{cat}/K_M$ DHF |
|---|---|---|---|---|---|
| WT | 17.5 | 62.93 | 31.21 | 41.13 | 2.4 |
| F98Y | 8.38 | 68.38 | 57.08 | 44.76 | 5.3 |
| H30N | 24.49 | 45.76 | 79.89 | 29.91 | 1.2 |
| H30N, F98Y | 11.24 | 39.98 | 51.17 | 26.1 | 2.3 |
| H149R | 63.54 | 42.44 | 303.4 | 27.74 | 0.4 |
| F98Y, H149R | 5.24 | 44.98 | 45.08 | 29.40 | 5.6 | mercaptoethanol, and 1 mg/mL BSA using 0.1 mM NADPH and 2 μg/mL enzyme. Inhibitor, in DMSO, was added to enzyme:NADPH mixture and allowed to incubate for 5 minutes before the addition of 0.1 mM DHF in 50 mM TES, pH 7.0. The inhibitor concentration and volume are based on the conditions that result in a 50% reduction in enzyme activity.

Enzyme kinetics were determined by Lineweaver-Burke plots generated by enzyme activity assays using 12.5-100 μM DHF with 20 μM NADPH for DHF $K_M$ and $V_{max}$ or 12.5-100 μM NADPH with 50 μM DHF for NADPH $K_M$. $K_M$ values were determined by non-linear regression analysis using GraphPad. Table 11 discloses the inhibitory constants, $K_i$ (nM), of PLA compounds against WT and mutant DHFR enzymes.

TABLE 11

| Cmpd | Sa(WT) | Sa(F98Y) | Sa(H30N) | Sa(H149R) | Sa(H30N, F98Y) | Sa(F98Y, H149R) |
|---|---|---|---|---|---|---|
| TMP | 3.43 | 14.68 | 6.89 | 240.8 | 595.1 | 1729 |
| A | 2.83 | 13.14 | 12.98 | 681.7 | 191.7 | 2059 |
| B | 2.53 | 3.01 | 33.25 | 1363 | 485.9 | 779.3 |
| 60 | 2.09 | 12.13 | 4.54 | 119.3 | 449.3 | 107.1 |
| C | 4.51 | 19.71 | 5.90 | 1563 | 820.3 | 878.5 |
| D | 2.68 | 8.57 | 16.72 | 1154 | 801.2 | 894.5 |
| E | 1.64 | 16.69 | 16.53 | 269.6 | 417.9 | 422.3 |
| F | 5.21 | 13.60 | 8.85 | 174.0 | 345.7 | 289.1 |
| 15 | 4.76 | 11.75 | 3.89 | 130.9 | 158.3 | 142.2 |
| 29 | 5.51 | 11.83 | 3.74 | 862.4 | 35.87 | 295.3 |
| 16 | 1.64 | 11.36 | 3.36 | 323.9 | 45.17 | 184.4 |
| 31 | 1.33 | 7.88 | 3.54 | 111.5 | 19.10 | 69.41 |
| 32 | 2.09 | 5.57 | 3.34 | 153.1 | 16.57 | 55.77 |

Example 12. PLA Inhibitors of Mutant S. Aureus

Compounds shown in Table 10 were evaluated as inhibitors of mutant S. Aureus. Compounds A-F have been previously disclosed.

TABLE 10

PLA Inhibitors of Mutant DHFR

| Cmpd | $R_p$ | $R_1$ | $R_2$ | $R_3$ | Ar |
|---|---|---|---|---|---|
| A | CH$_3$ | H | OCH$_3$ | H | Pyridine |
| B | CH$_3$ | H | OCH$_2$ | OCH$_2$ | Pyridine |
| 60 | H | H | OCH$_3$ | OCH$_3$ | Pyridine |
| C | CH$_3$ | OCH$_3$ | H | H | Pyridine |
| D | R—CH$_3$ | H | OCH$_3$ | H | Pyridine |
| E | R—CH$_3$ | OCH$_3$ | H | H | Pyridine |
| F | R—CH$_3$ | H | OCH$_2$ | OCH$_2$ | Pyridine |
| 15 | H | OCH$_3$ | H | H | p-COOH |
| 29 | S—CH$_3$ | OCH$_3$ | H | H | p-COOH |
| 16 | H | H | OCH$_3$ | H | p-COOH |
| 31 | R—CH$_3$ | H | OCH$_3$ | H | p-COOH |
| 32 | S—CH$_3$ | H | OCH$_3$ | H | p-COOH |

The inhibitory effect of the Table 10 compounds was determined using the following DHFR binding assay. Enzyme inhibition assays were performed by monitoring the rate of NADPH oxidation by DHFR via absorbance at 340 nm at room temperature in assay buffer containing 20 mM TES, pH 7.0, 50 mM KCl, 0.5 mM EDTA, 10 mM beta- All TABLE 10 compounds exhibit good potency ($K_i$ values less than 15 nM) against the single mutant enzymes Sa (F98Y) and Sa(H30N) with only minor losses relative to wild-type (Table 11). Compound B lost the greatest affinity for the Sa(H30N) enzyme with a 12.6-fold loss. Activity against the single mutant Sa(H149R), however, was more compromised. TMP loses activity against the Sa(H149R) mutant by 69-fold. The PLAs possess a range of affinity for this enzyme, ranging from compound 12 with a $K_i$ value of 185 nM to compound B with a $K_i$ value of 1649 nM. Interestingly, compound 3 with unconstrained 3' and 4' methoxy groups maintained reasonable affinity (144 nM) when compared to compound B, showing that flexibility may be critical for affinity to the mutant enzymes. Against the double mutant, Sa (F98Y, H30N), TMP loses 130-fold in affinity. In general, the dioxalane compounds (B and F) as well as compounds C-E lose significant affinity for the Sa (F98Y, H30N) double mutant enzyme(180 to 300-fold loss).

The design of compounds 15-16, 29, 31-32 is predicated on a possible interaction with a conserved Arginine to provide compensatory interactions in these mutant enzymes. Pleasingly, compounds 29, 16, and 31-32 show much greater affinity for the double mutant Sa (F98Y, H30N) enzyme with $K_i$ values ranging from 16-45 nM. Maintaining activity against the double mutant Sa (F98Y, H149R) enzyme is clearly more challenging as compounds A-F, 60 and 15 and TMP show $K_i$ values of 107-2059 nM. However, compounds 31 and 32 show significant inhibition for this enzyme, with $K_i$ values of 69 and 55 nM, respectively. Again, it appears that the presence of the ionized carboxylates may provide critical additional interactions to compensate for reduced contacts elsewhere in the complex.

The compounds were also tested for inhibition of the growth of wild-type and mutant strains of *S. aureus* (Sa (F98Y), Sa(H30N), Sa(H149R), Sa(H30N, F98Y) and Sa(F98Y/H149R) (Table 12). The antibacterial activity of TMP was clearly crippled by even the single mutations and reached a 50-100 μg/mL MIC value against the double mutant strains. PLAs A-F, 60, 15, and 29 were more potent against the wild-type strain than TMP and many were more potent against the single mutants (MIC values between 0.078 and 5 μg/mL). However, PLAs A-F, 60, 15, and 29 also suffered significant losses against the strains with double mutations in DHFR. PLAs 16, 31, and 32 have superior activity against the wild-type strain as well as strains with both single and double mutants.

TABLE 12

| Cmpd | Sa43300 | Sa(F98Y) | Sa(H30N) | Sa(H149R) | Sa(H30N, F98Y) | Sa(F98Y, H149R) |
|---|---|---|---|---|---|---|
| TMP | 0.3125 | 10 | 2.5 | 2.5 | 50 | 100 |
| A | 0.0781 | 2.5 | 2.5 | 2.5 | 20 | 80 |
| B | 0.0781 | 1.25 | 5 | 5 | 40 | 40 |
| 60 | 0.0195 | 0.625 | 0.625 | 0.625 | 20 | 40 |
| C | 0.625 | 2.5 | 2.5 | 2.5 | 20 | 40 |
| D | 0.0391 | 0.625 | 0.625 | 0.625 | 40 | 20 |
| E | 0.0195 | 1.25 | 0.625 | 1.25 | 10 | 20 |
| F | 0.0195 | 1.25 | 2.5 | 2.5 | 20 | 20 |
| 15 | 0.0195 | 0.1563 | 0.1563 | 0.1564 | 6.25 | >50 |
| 29 | 0.0391 | 0.1563 | 0.1563 | 0.0781 | >40 | >40 |
| 16 | 0.0195 | 0.1563 | 0.1563 | 0.1563 | 5 | 10 |
| TMP | 0.3125 | 10 | 2.5 | 2.5 | 50 | 100 |
| 31 | 0.0098 | 0.0781 | 0.0781 | 0.0391 | 1.25 | 2.5 |
| 32 | 0.0098 | 0.0781 | 0.0781 | 0.0781 | 1.25 | 1.25 |

What is claimed is:

1. A compound of the formula I

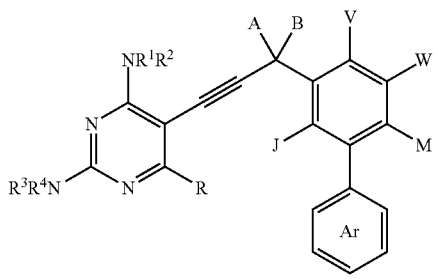

(I)

or a pharmaceutically acceptable salt thereof, wherein:
R is H, hydroxyl, $C_1$-$C_6$alkyl, or $C_1$-$C_6$alkoxy;
$R^1$, $R^2$, $R^3$, and $R^4$ are independently chosen from H, $C_1$-$C_6$alkyl, and cycloalkyl;
A and B are independently chosen from H, hydroxyl, $C_1$-$C_6$alkyl, and $C_1$-$C_6$alkoxy;
one of V and W is methoxy and the other is chosen from H, $C_1$-$C_6$alkyl, and $C_1$-$C_6$alkoxy;
J and M are independently selected from H, halogen, hydroxyl, nitro, cyano, —COOH, —CHO, —CONH$_2$, cycloalkyl, or $C_1$-$C_6$alkyl in which any methylene (—CH$_2$) is optionally replaced by O, NH, N($C_1$-$C_6$alkyl), S, SO$_2$, C(O)O, OC(O), or C(O), and which is optionally substituted with hydroxyl, amino, or halogen;
W and M may be joined to form a 5- or 6-membered carbocyclic ring or a 5- or 6-membered heterocyclic ring that contains 1, 2, or 3 heteroatoms independently chosen from N, O, and S; and the Ar ring is a phenyl, pyridyl, or pyrimidinyl ring substituted with at least one —COOH, or —CH$_2$COOH, group and optionally substituted with one or more substituents independently chosen from halogen, hydroxyl, amino, $C_1$-$C_6$alkyl, $C_1$-$C_6$alkoxy, $C_1$-$C_2$haloalkyl, and $C_1$-$C_2$haloalkoxy.

2. The compound or pharmaceutically acceptable salt of claim 1, wherein
R is methyl or ethyl;
A is hydrogen;
B is hydrogen or $C_1$-$C_6$alkyl; and
one of V and W is methoxy and the other is H.

3. The compound or pharmaceutically acceptable salt of claim 1, wherein
R is methyl or ethyl;
A is hydrogen;
B is hydrogen or $C_1$-$C_6$alkyl; and
W and M are joined to form a 5-membered heterocyclic ring containing 2 oxygen atoms.

4. The compound or pharmaceutically acceptable salt of claim 1, wherein
$R_1$, $R_2$, $R_3$, and $R_4$ are H.

5. The compound or pharmaceutically acceptable salt claim 2, wherein
J and M are independently selected from H, halogen, hydroxyl, $C_1$-$C_6$alkyl, $C_1$-$C_6$alkoxy, $C_1$-$C_2$haloalkyl, and $C_1$-$C_2$haloalkoxy.

6. The compound or pharmaceutically acceptable salt of claim 1, wherein A is H and B is methyl.

7. The compound or pharmaceutically acceptable salt of any one of claim 2, wherein J and M are both H.

8. The compound or pharmaceutically acceptable salt of claim 1, where the Ar ring is substituted with one —COOH substituent in the para position and optionally substituted with one or more substituents independently chosen from halogen, hydroxyl, amino, $C_1$-$C_6$alkyl, $C_1$-$C_6$alkoxy, $C_1$-$C_2$haloalkyl, and $C_1$-$C_2$haloalkoxy.

9. The compound or pharmaceutically acceptable salt of claim 1, where the Ar ring is substituted with one —COOH substituent in the meta position and optionally substituted with one or more substituents independently chosen from halogen, hydroxyl, amino, $C_1$-$C_6$alkyl, $C_1$-$C_6$alkoxy, $C_1$-$C_2$haloalkyl, and $C_1$-$C_2$haloalkoxy.

10. The compound or pharmaceutically acceptable salt of claim 1, where the Ar ring is substituted with one —COOH substituent in the ortho position and optionally substituted with one or more substituents independently chosen from halogen, hydroxyl, amino, $C_1$-$C_6$alkyl, $C_1$-$C_6$alkoxy, $C_1$-$C_2$haloalkyl, and $C_1$-$C_2$haloalkoxy.

11. The compound or pharmaceutically acceptable salt of claim 1, wherein the Ar ring is a substituted phenyl ring.

12. A compound or pharmaceutically acceptable salt of of the formula I-A

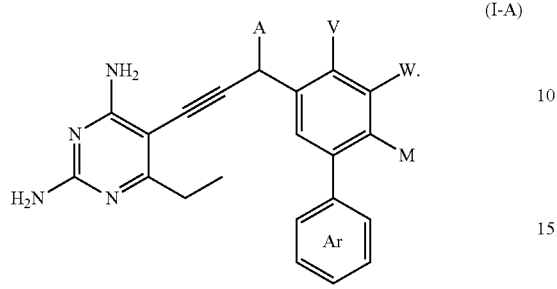

(I-A)

(I-A) wherein the compound is selected from the compounds listed in

TABLE I

| Cpd | A | V | W | M | Ar |
|---|---|---|---|---|---|
| 13 | H | OCH₃ | H | H | o-COOH phenyl |
| 14 | H | OCH₃ | H | H | m-COOH phenyl |
| 15 | H | OCH₃ | H | H | p-COOH phenyl |
| 16 | H | H | OCH₃ | H | p-COOH phenyl |
| 29 | S—CH₃ | OCH₃ | H | H | p-COOH phenyl |
| 30 | R—CH₃ | OCH₃ | H | H | p-COOH phenyl |
| 31 | R—CH₃ | H | OCH₃ | H | p-COOH phenyl |
| 32 | S—CH₃ | H | OCH₃ | H | p-COOH phenyl |
| 33 | S—CH₃ | OCH₃ | H | H | p-COOCH₃ phenyl |
| 34 | R—CH₃ | OCH₃ | H | H | p-COOCH₃ phenyl |
| 35 | CH₃ | H | —O—CH₂—O— | | (HOOC-CH₂-C₆H₄-) |
| 36 | CH₃ | H | —O—CH₂—O— | | p-OH-phenyl |
| 37 | H | H | —O—CH₂—O— | | p-OH-phenyl |
| 38 | H | H | —O—CH₂—O— | | 3-F,4-OH-phenyl |
| 39 | H | H | —O—CH₂—O— | | 3,5-di-F,4-OH-phenyl |
| 40 | H | H | —O—CH₂—O— | | 3,5-di-F,4-OCH₃-phenyl |
| 41 | S—CH₃ | H | —O—CH₂—O— | | p-COOH-phenyl |
| 42 | R—CH₃ | H | —O—CH₂—O— | | p-COOH-phenyl |
| 43 | CH₃ | H | —O—CH₂—O— | | 2,3,5-tri-F,4-OH-phenyl |
| 44 | CH₃ | H | —O—CH₂—O— | | 2,3,5,6-tetra-F, 4-OH-phenyl |
| 45 | CH₃ | H | —O—CH₂—O— | | 3-CN, 4-OH-phenyl |
| 46 | CH₃ | H | —O—CH₂—O— | | 4-CH₃SO₂HN-phenyl |
| 47 | CH₃ | H | —O—CH₂—O— | | 4-CH₃HNSO₂-phenyl |
| 48 | CH₃ | H | —O—CH₂—O— | | (HO-C(O)-pyridyl) |
| 49 | CH₃ | H | —O—CH₂—O— | HO—NH | (HO-NH-C(O)-C₆H₄-) |
| 50 | CH₃ | H | —O—CH₂—O— | | 3,4,-di-OH-phenyl |
| 51 | CH₃ | H | —O—CH₂—O— | | (4-oxo-pyridin-1-yl) |

TABLE 1-continued

TABLE 1

| Cpd | A | V | W | M | Ar |
|---|---|---|---|---|---|
| 52 | H | H | OMe | H | p-(HOOC-CH2) phenyl |
| 53 | H | H | OMe | H | p-(H2N-CH(COOH)) phenyl |
| 54 | CH | H | —O—CH2—O— | | N-methyl-imidazol-5-yl |
| 55 | R—CH3 | H | —O—CH2—O— | | pyrid-4-yl |
| 56 | H | OCH3 | H | H | N-methyl-imidazol-5-yl |
| 57 | R—CH3 | OCH3 | H | H | pyrid-4-yl |
| 58 | R—CH3 | H | OCH3 | H | p-COOH phenyl |
| 59 | H | H | OCH3 | H | p-COOH phenyl |
| 60 | H | H | OCH3 | OCH3 | 4-Pyridyl |

13. The compound or pharmaceutically acceptable salt of claim 12, wherein the compound is

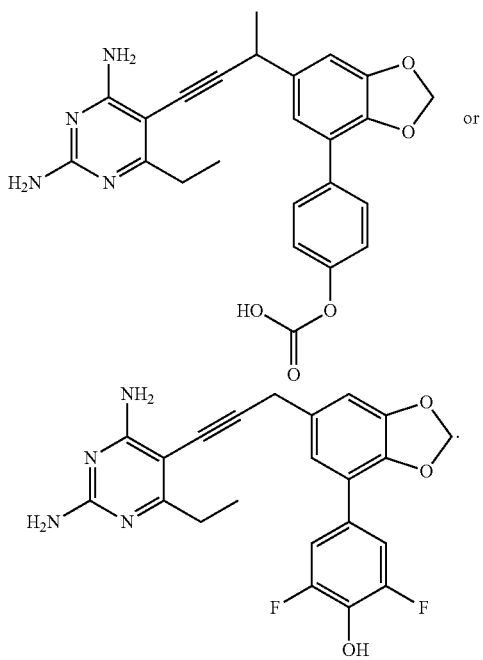

14. A pharmaceutical composition comprising a compound or pharmaceutically acceptable salt thereof of claim 1, and a pharmaceutically acceptable carrier.

15. A method of treating a bacterial infection or a fungal infection in a patient comprising administering a therapeutically effective amount of a compound or salt of claim 1 to the patient.

16. The method of claim 15, additionally comprising administering an additional antibacterial compound that is not a compound of formula I or salt thereof to the patient.

17. The method of claim 15, wherein the bacterial infection is a Gram negative bacterial infection.

18. The method of claim 15, wherein the bacterial infection is a *S. aureus* infection.

UNITED STATES PATENT AND TRADEMARK OFFICE
CERTIFICATE OF CORRECTION

| | | Page 1 of 1 |
|---|---|---|
| PATENT NO. | : 10,870,625 B2 | |
| APPLICATION NO. | : 16/068262 | |
| DATED | : December 22, 2020 | |
| INVENTOR(S) | : Dennis Wright et al. | |

It is certified that error appears in the above-identified patent and that said Letters Patent is hereby corrected as shown below:

In the Specification

Column 1, after Line 9, add:
--STATEMENT REGARDING FEDERALLY SPONSORED RESEARCH
This invention was made with government support under AI104841, and AI111957 awarded by the National Institutes of Health. The government has certain rights in the invention.--

Signed and Sealed this
Nineteenth Day of August, 2025

Coke Morgan Stewart
*Acting Director of the United States Patent and Trademark Office*